United States Patent
Ren et al.

(10) Patent No.: US 8,828,713 B2
(45) Date of Patent: Sep. 9, 2014

(54) SENSORS USING HIGH ELECTRON MOBILITY TRANSISTORS

(75) Inventors: Fan Ren, Gainesville, FL (US); Stephen John Pearton, Gainesville, FL (US); Tanmay Lele, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 249 days.

(21) Appl. No.: 12/966,531

(22) Filed: Dec. 13, 2010

(65) Prior Publication Data

US 2011/0074381 A1    Mar. 31, 2011

Related U.S. Application Data

(63) Continuation of application No. 12/724,117, filed on Mar. 15, 2010, which is a continuation-in-part of application No. PCT/US2008/076885, filed on Sep. 18, 2008.

(60) Provisional application No. 60/973,302, filed on Sep. 18, 2007, provisional application No. 60/975,907, filed on Sep. 28, 2007, provisional application No. 60/982,310, filed on Oct. 24, 2007.

(51) Int. Cl.
*G01N 27/00* (2006.01)

(52) U.S. Cl.
USPC ........... 435/287.2; 435/283.1; 435/287.1; 435/7.1; 436/518; 436/524; 436/525; 422/68.1; 422/82.01

(58) Field of Classification Search
USPC .......... 435/283.1, 287.1, 287.2, 7.1; 436/518, 436/524, 525; 422/68.1, 82.01
See application file for complete search history.

(56) References Cited

U.S. PATENT DOCUMENTS

| | | | |
|---|---|---|---|
| 4,734,750 | A | 3/1988 | Okamura et al. |
| 5,368,707 | A | 11/1994 | Henkens et al. |
| 6,338,968 | B1 | 1/2002 | Hefti |
| 6,368,795 | B1 | 4/2002 | Hefti |
| 6,485,905 | B2 | 11/2002 | Hefti |
| 6,534,801 | B2 | 3/2003 | Yoshida |

(Continued)

OTHER PUBLICATIONS

International Patent Application No. PCT/US2008/076885, Written Opinion of the International Searching Authority and International Search Report, completed May 13, 2009.

(Continued)

*Primary Examiner* — Melanie Y Brown
(74) *Attorney, Agent, or Firm* — Saliwanchik, Lloyd & Eisenschenk, P.A.

(57) ABSTRACT

Embodiments of the invention include sensors comprising high electron mobility transistors (HEMTs) with capture reagents on a gate region of the HEMTs. Example sensors include HEMTs with a thin gold layer on the gate region and bound antibodies; a thin gold layer on the gate region and chelating agents; a non-native gate dielectric on the gate region; and nanorods of a non-native dielectric with an immobilized enzyme on the gate region. Embodiments including antibodies or enzymes can have the antibodies or enzymes bound to the Au-gate via a binding group. Other embodiments of the invention are methods of using the sensors for detecting breast cancer, prostate cancer, kidney injury, glucose, metals or pH where a signal is generated by the HEMT when a solution is contacted with the sensor. The solution can be blood, saliva, urine, breath condensate, or any solution suspected of containing any specific analyte for the sensor.

20 Claims, 21 Drawing Sheets

(56) References Cited

U.S. PATENT DOCUMENTS

| | | |
|---|---|---|
| 7,182,914 B2* | 2/2007 | Lai et al. .................... 422/82.01 |
| 2001/0018058 A1* | 8/2001 | Reed et al. ................. 424/277.1 |
| 2002/0018990 A1* | 2/2002 | Billing-Medel et al. .......... 435/6 |
| 2002/0127580 A1* | 9/2002 | Quay ................................. 435/6 |
| 2003/0138872 A1* | 7/2003 | Kawasaki et al. ............... 435/25 |
| 2005/0053524 A1* | 3/2005 | Keersmaecker et al. ....... 422/88 |
| 2005/0263790 A1 | 12/2005 | Moon et al. |
| 2006/0205161 A1* | 9/2006 | Das et al. ...................... 438/284 |
| 2006/0223170 A1* | 10/2006 | Kamahori et al. ......... 435/287.2 |
| 2006/0228723 A1* | 10/2006 | Bradley et al. .................... 435/6 |
| 2007/0018198 A1* | 1/2007 | Brandes et al. ............... 257/183 |
| 2007/0046287 A1* | 3/2007 | Vervaeke et al. ............. 324/251 |
| 2008/0283875 A1* | 11/2008 | Mukasa et al. ................ 257/253 |

OTHER PUBLICATIONS

Kang, B.S., et al. "Electrical detection of immobilized proteins with ungated AlGaN/GaN high-electron-mobility Transistors," Applied Physics Letters, vol. 87, Issue 023508, 2005.

Kang, B.S., et al. "Electrical detection of deoxyribonucleic acid hybridization with AlGaN/GaN high electron mobility transistors," Applied Physics Letters, vol. 89, Issue 122102, 2006.

Kang, B.S., et al. "Electrical detection of biomaterials using AlGaN/GaN high electron mobility transistors," Journal of Applied Physics, vol. 104, Issue 031101, 2008.

Chen, K.H., et al. "c-erB-2 sensing using AlGaN/GaN high electron mobility transistors for breast cancer detection," Applied Physics Letters, vol. 92, Issue 192103, 2008.

Kang, B.S., et al. "Prostate specific antigen detection using AlGaN/GaN high electron mobility transistors," Applied Physics Letters, vol. 91, Issue 112106, 2007.

Wang, H.T., et al. "Electrical detection of kidney injury molecule-1 with AlGaN/GaN high electron mobility transistors," Applied Physics Letters, vol. 91, Issue 222101, 2007.

Chen, K.H., et al. "Log Hg(II) ion concentration electrical detection with AlGaN/GaN high electron mobility transistors," Sensors and Actuators B 134, pp. 386-389, 2008.

Wang, H.T., et al. "Fast electrical detection of Hg(II) ions with AlGaN/GaN high electron mobility transistors," Applied Physics Letters, vol. 91, Issue 042114, 2007.

Wang, H.T., et al. "Selective Detection of Hg(II) Ions from Cu(II) and Pb(II) Using AlGaN/GaN High Electron Mobility Transistors," Electrochemical and Solid-State Letters, vol. 10, Issue 11, 2007.

Kang, B.S., et al. "pH sensor using AlGaN/GaN high electron mobility transistors with $Sc_2O_3$ in the gate region," Applied Physics Letters, vol. 91, Issue 012110, 2007.

Kang, B.S., et al. "Role of Gate Oxide in AlGaN/GaN High-Electron-Mobility Transistor pH Sensors," Journal of Electronic Materials, vol. 37, No. 5, 2008.

Kang, B.S., et al. "Enzymatic glucose detection using ZnO nanorods on the gate region of AlGaN/GaN high electron mobility transistors," Applied Physics Letters, vol. 91, Issue 252103, 2008.

Chu, B.H., et al. "Enzyme-based lactic acid detection using AlGaN/GaN high electron mobility transistors with ZnO nanorods grown on the gate region," Applied Physics Letters, vol. 93, Issue 042114, 2008.

U.S. Appl. No. 12/664,022, Claims, filed Dec. 12, 2009.

\* cited by examiner

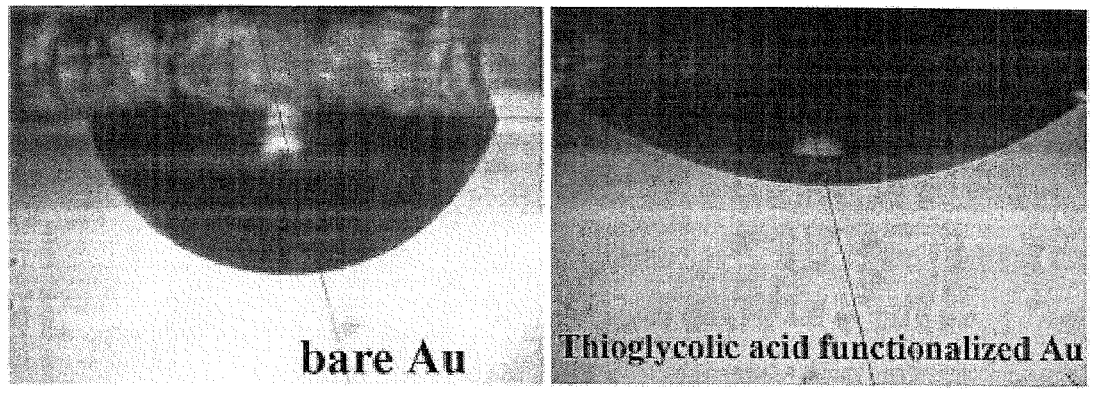
Figure 5A                    Figure 5B
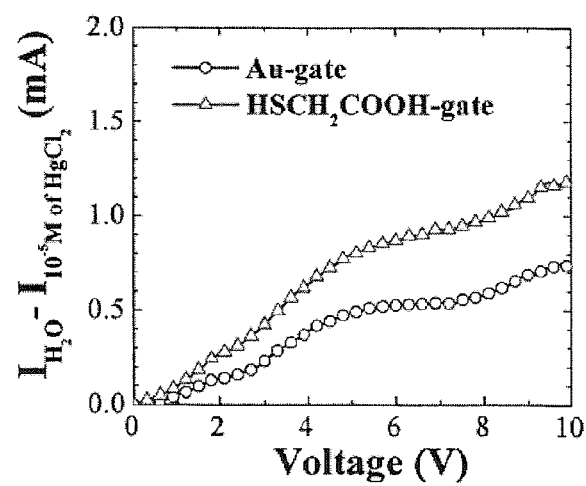
Figure 6

SENSORS USING HIGH ELECTRON MOBILITY TRANSISTORS

CROSS-REFERENCE TO RELATED APPLICATIONS

This application is a continuation of U.S. application Ser. No. 12/724,117, filed Mar. 15, 2010, which is a continuation-in-part of International Patent Application No. PCT/US2008/076885, filed Sep. 18, 2008, which claims the benefit of U.S. Provisional Application Ser. No. 60/973,302, filed Sep. 18, 2007, U.S. Provisional Application Ser. No. 60/975,907, filed Sep. 28, 2007, and U.S. Provisional Application Ser. No. 60/982,310, filed Oct. 24, 2007, all of which are hereby incorporated by reference herein in their entirety, including any figures, tables, or drawings.

BACKGROUND OF THE INVENTION

Chemical sensors can be used to analyze a wide variety of environmental and bodily gases, aerosols, and fluids for properties of interest. For example, exhaled breath condensate (EBC) is widely known to be a diagnostically important bodily fluid that can be safely collected. In particular, the breath from deep within the lungs (alveolar gas) is in equilibrium with the blood, and therefore the concentrations of molecules present in the breath is highly correlated with those found in the blood at any given time. Analysis of molecules in exhaled breath condensate is a promising method that can provide information on the metabolic state of the human body, including certain signs of cancer, respiratory disease, and liver and kidney function. Several different analysis methods including gas chromatography (GC), chemiluminescence, selected ion flow tube (SIFT), and mass spectroscopy (MS) have been used to measure different exhaled biomarkers, including hydrogen peroxide, nitrogen oxide, aldehydes, and ammonia. However, these methods vary significantly in sensitivity.

Another example of sensing application using body fluid is detecting breast cancer with saliva. The mortality rate in breast cancer patients can be reduced by increasing the frequency of screening. The overwhelming majority of patients are screened for breast cancer by mammography. This procedure involves a high cost to the patient. Moreover, the use of invasive radiation limits the frequency of screening. Recent evidence suggests that salivary testing for markers of breast cancer may be used in conjunction with mammography. Saliva based diagnostics for the protein c-erbB-2, a prognostic breast marker assayed in tissue biopsies of women diagnosed with malignant tumors, has shown tremendous potential. Soluble fragments of the c-erbB-2 oncogene and the cancer antigen 15-3 were found to be significantly higher in the saliva of women who had breast cancer than in those patients with benign tumors. Another recent study concluded that epidermal growth factor (EGF) is a promising marker in saliva for breast cancer detection.

Pilot studies indicate that the saliva test is both sensitive and reliable, and is potentially useful in initial detection and follow-up screening for breast cancer. However, currently saliva samples are typically obtained from a patient in a dentist's office then sent to a testing lab; it typically takes a few days to get the test results.

To fully realize the potentials of sensors for environmental, health related, chemical and biomedical applications, technologies are needed that will enable easy, sensitive, and specific detection of chemical or biomolecules at home or elsewhere. It is also desirable that a testing device allows concomitant wireless data transmission into preprogrammed destinations, such as transmitting breast cancer testing results to a doctor or clinic. If inexpensive technologies that can detect and wirelessly transmit testing results for environmental, health related, chemical and biomedical applications can be developed, early diagnosis of cancers or disease can significantly lower mortality and the cost of health care. In addition, real-time wireless remote sensing for chemicals in the environment may reduce the incidence of disasters by alerting to a chemical hazard.

BRIEF SUMMARY

High electron mobility transistors (HEMTs), and the particularly exemplified AlGaN/GaN HEMTs, are a key component of the sensors according to embodiments of the invention. AlGaN/GaN HEMTs with specified surface functionality perform as sensors to detect various molecules, including biomarkers, of interest in bodily fluid samples.

For example, embodiments of the invention are directed to surface functionalized AlGaN/GaN HEMT based sensors that can detect prostate cancer, breast cancer, pH, mercury, copper, glucose, and/or evidence of acute kidney injury or renal failure in samples of exhaled breath condensate, saliva, urine, blood, or other fluids. In certain embodiments, the devices according to the invention can wirelessly transmit results in order to facilitate rapid analysis of the results.

One embodiment of the invention is a device for detecting breast cancer that includes a gold-gated AlGaN/GaN HEMT functionalized with an antibody to an antigen associated with breast cancer as the capture reagent. A method for detection of breast cancer in a saliva sample is also exemplified.

A second embodiment of the invention is a device for detection of heavy metals. The device includes a gold-gated AlGaN/GaN HEMT functionalized with a chelating agent as the capture reagent. A method for detection of heavy metals in solution comprises analyzing a sample with a gold-gated AlGaN/GaN HEMT functionalized with a chelating agent such as thioglycolic acid ($HSCH_2COOH$), cysteamine ($NH_2CH_2CH_2SH$), 1,2-ethanedithiol ($HSCH_2CH_2SH$), dimercaprol (BAL), diaminoethanetetraacetic acid (EDTA), 2,3-bis-sulfanylbutanedioic acid (DMSA), or 2,3-dimercapto-1-propanesulfonic acid (DMPS).

A third embodiment of the invention is a device for detecting changes in pH. The device includes an AlGaN/GaN HEMT having a gate dielectric coating, for example a thin $Sc_2O_3$ layer, used as the capture reagent. The device can further include a cooling element to obtain exhaled breath condensates for testing. A method for detecting the pH of exhaled breath condensate is also disclosed.

A fourth embodiment is a device for detecting prostate cancer using a capture reagent formed via carboxylate succinimdyl ester bound prostate specific antigen (PSA) antibodies linked to thioglycolic acid immobilized on a gold-coated gate of an AlGaN/GaN HEMT. A method of detecting prostate cancer by analysis of PSA in a sample is also disclosed.

A fifth embodiment is a device for detecting acute kidney injury or renal failure where a gold-gated AlGaN/GaN HEMT functionalized with highly specific KIM-1 antibodies through a self-assembled monolayer of thioglycolic acid acts as the detector. A method to detect KIM-1 in a sample is also disclosed.

A sixth embodiment is a device for detecting glucose in exhaled breath condensate. The device includes an AlGaN/GaN HEMT having a nanorod array selectively grown on the gate area of the HEMT that immobilizes glucose oxidase (GOx). The nanorods may be, for example, metal oxide and nitride based nanorods. A method to detect glucose in exhaled breath condensate is also disclosed.

In accordance with embodiments of the present invention, normalized detection is provided.

BRIEF DESCRIPTION OF THE FIGURES

FIGS. 5A and 5B are photographs of the contact angle of a water drop on the surface of bare Au (FIG. 5A) and thioglycolic acid functionalized Au (FIG. 5B).

FIG. 6 illustrates a plot of changes in HEMT drain-source current for bare Au-gate and Au-gate with thioglycolic acid functionalization exposed to $10^{-5}$ M $Hg^{2+}$ ion solutions when using an AlGaN/GaN HEMT sensor of the invention.

DETAILED DISCLOSURE

Figure 1A:
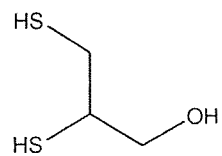
FIGS. 1A-1D show the chemical structures for BAL, EDTA, DMSA, and DMPS, respectively.
Figure 1B:
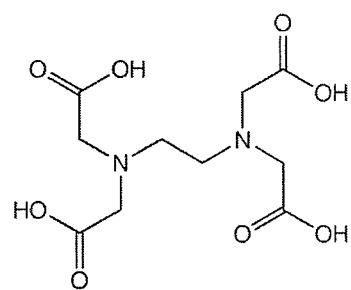
Figure 1C:
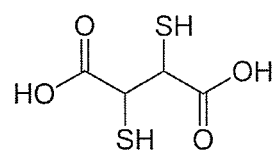
Figure 1D:
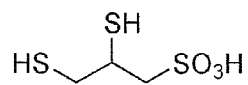

One shortcoming of HEMT sensors has been a lack of selectivity to different analytes due to the chemical inertness of the HEMT surface. Sensor devices according to embodiments of the invention solve this sensitivity problem by functionalization of the gate surface with capture reagents.

The sensor devices of the subject invention can be used with a variety of samples having environmental and/or bodily origins, including saliva, urine, blood, breath (including exhaled breath condensates) and other samples. For example, in certain embodiments of the invention, mercury or cancer detection is improved. Additionally, sensors according to embodiments of the invention can be re-used, without substantial diminishment of efficacy.

Group III-N based wide bandgap semiconductors are used as sensitive chemical sensors, especially when made with piezoelectric materials. GaN/AlGaN high electron mobility transistors (HEMTs) form a high density electron sheet carrier concentration channel induced by piezoelectric polarization of the strained AlGaN layer and spontaneous polarization of the different ionic strength between the GaN and AlGaN layer. The conducting 2-dimensional electron gas (2DEG) channel of GaN/AlGaN based HEMTs is very close to the surface and extremely sensitive to the ambient environment, allowing enhanced detection sensitivity.

GaN-based wide energy bandgap semiconductor material systems are extremely chemically stable; this stability is minimally degraded by adsorbed cells. The bond between Ga and N is ionic and proteins easily attach to the GaN surface. This is an important factor for preparation of a sensitive biosensor having a useful lifetime.

The HEMT sensors of the subject invention can be used to detect, for example, gases, ions, pH values, proteins, and/or DNA with good selectivity by modification of the surface in the gate region of the HEMT. HEMT structures can be used in microwave power amplifiers as well as gas and liquid sensors because of their high 2DEG mobility and saturation velocity.

In certain embodiments of the invention, a 2-dimensional electron gas (2DEG) at the interface of AlGaN/GaN heterostructures is formed through the hetero junction of AlGaN and GaN, which have different bandgaps. The 2DEG channel is connected to an Ohmic-type source and drain contacts. The source-drain current is modulated by a third contact, a Schottky-type gate, on the top of the 2DEG channel. For sensing applications, the third contact is affected by the sensing environment, i.e. the sensing targets change the charges on the gate region and the behavior of the gate. When analytes accumulate on the gate area, the net charge on the HEMT surface is changed. The net surface charge alters the 2DEG concentration. This electrical detection technique is simple, fast, and convenient.

The detecting signal from the gate can be amplified through the drain-source current, making the sensor very sensitive. The electric signal can be easily quantified, recorded and transmitted, unlike fluorescence detection methods that need human inspection and are difficult to be precisely quantified and transmitted.

Gateless HEMT structures can distinguish liquids with different polarities and can quantitatively measure pH over a broad range. The sensing mechanism for chemical adsorbates in piezoelectric materials originates from compensation of the polarization induced bound surface charge by interaction with the polar molecules in liquids. In gateless AlGaN/GaN heterostructure transistors, the native oxide on the nitride surface is responsible for the pH sensitivity of the response to electrolyte solutions. By coating a thin non-native metal oxide, for example $Sc_2O_3$, on the gate sensing area, more sensitive and reproducible hydronium ion, $H_3O^+$ (pH) sensing is achieved. In embodiments of the invention, the non-native metal oxide on the gate sensing area of the HEMT is referred to as a gate dielectric layer.

Usually, it is difficult to control the compositions and thickness of native oxides. For embodiments of the invention, a metal oxide such as $Sc_2O_3$ is grown by a molecule beam epitaxy system with excellent composition and thickness control. In certain embodiments of the invention, other gate dielectric layers, such as metal nitrides, can be used rather than metal oxide dielectric layers. The pH response of an oxide/nitride interface can be modeled in terms of formation of hydroxyl groups that lead to a hydronium ion concentration (pH) dependent net surface change with a resulting change in voltage drop at the semiconductor/liquid interface.

According to one embodiment of the subject invention, real-time detection of the pH of exhaled breath uses a breathing tube and ice bath with an AlGaN/GaN HEMT. The breathing tube samples exhaled breath and the ice bath condenses the sample that is applied to the AlGaN/GaN HEMT.

In one embodiment, the device may include an AlGaN/GaN HEMT that is operably coupled to a thermal electric cooling device, which condenses exhaled breath samples. The thermal water vapor and volatile organic compounds from the exhaled breath condensate change the surface charge on the HEMT, thus changing the current flowing in the HEMT device for a fixed applied bias voltage. In one embodiment, an exhaled breath condensate (EBC) biosensor of the present disclosure can be handheld, low in cost, and capable of real-time detection without consumable carrier gases.

Biologically modified field effect transistors (bioFETs), either at conventional or nano-dimensions, can directly detect biochemical interactions in aqueous solutions for a wide variety of biosensing applications. To enhance the practicality of bioFETs, a device according to embodiments of the invention is sensitive to biochemical interactions on its surface that is functionalized to probe specific biochemical interactions. In one embodiment, the device is stable in aqueous solutions across a range of pH and salt concentrations. In other embodiments, the gate region of the device is covered with capture reagents for molecules of interest. The conductance of the device changes as interaction occurs between these capture reagents and appropriate species (the molecules of interest) in a sample.

In one embodiment of the invention, a saliva based breast cancer detector is functionalized in the gate region with chemicals that can bind (or otherwise interact with) breast cancer markers. The gate region of the HEMT can be a few nanometers to a few millimeters in size. An array of the HEMT sensors can be fabricated on a single chip. Each HEMT can be functionalized with a capture reagent for a breast cancer marker. A set of testing results can be obtained from a series of different capture reagents. Simultaneous breast cancer detections with different capture reagents can increase the accuracy of the cancer detection.

Because the surface of AlGaN is extremely inert and difficult to oxidize, a thin layer of gold of, for example, about 5 nm can be used as an intermediate layer between AlGaN and certain capture reagents used in embodiments of the invention. A molecule containing a thiol group can be immobilized on the Au surface by an Au—S bond. Other functional groups can then bind with a capture reagent. These other functional groups can be, for example, alcohol, aldehyde, carboxylic acid, phosphate or amine groups. The immobilized capture reagents can bind with breast cancer biomarkers (or other target molecules). In one embodiment an Au-gated GaN/AlGaN HEMT is used as a sensor for the detection of breast cancer markers in a saliva sample.

In some embodiments, sensors comprise chemical adsorbates on AlGaN/GaN HEMTs where detection originates from compensating or inducing charges at the AlGaN/GaN interface due to polar molecules in the liquids bonded to the AlGaN/GaN surface. In certain embodiments, the device is functionalized at the AlGaN/GaN/HEMT surface having an Au-coated gate region by chemicals selected for their interaction with a target being detected.

According to one embodiment of the invention, thioglycolic acid can be used to assist in functionalizing an AlGaN/GaN HEMT sensor. For example, a self-assembled monolayer of thioglycolic acid can be adsorbed onto an Au-gate due to interaction between gold and the thiol-group. Following placement of the thioglycolic acid on the sensor surface, a specific functionality of interest may be conjugated to the surface, where the functionality is a capture reagent for a specific target being sensed.

According to certain embodiments of the invention, a sensor can include a synthetic or natural compound as a capture reagent with the ability to associate with a desired target molecule, such as a biomarker. The capture reagent associates with the desired target molecule by interacting with the target molecule in a way that is detectable by the HEMT. The capture reagent may associate with the target molecule by binding with the target molecule, but embodiments are not limited thereto.

The capture reagents of certain embodiments of the invention include naturally occurring and/or synthetic compounds that preferably display high specificity and sensitivity to a target molecule of interest. Suitable compounds include, but are not limited to, antibodies, proteins, and aptamers that can associate with a biomarker. The term "biomarker" refers to a biochemical in the body with a particular molecular trait that makes it useful for diagnosing a condition, disorder, or disease, and for measuring or indicating the effects or progress of a condition, disorder, or disease. Antibodies are protein molecules that are typically composed of heavy and light polypeptide amino acid chains held together with disulfide bonds. These highly specialized proteins are able to recognize and selectively bind certain types of antigen molecules. In embodiments of the invention, a sensor employs antibodies to detect specific antigens.

In an embodiment of the invention, the chemistry of the system occurs along a conductive layer, for example, a gold layer. The conductive layer supports the propagation of a high frequency test signal and is capable of binding to (or otherwise associating with) a target molecule, which is typically an antigen or other analyte. In one embodiment, thioglycolic acid bonds the Au layer to antibodies for breast cancer antigens including (but not limited to) EGF, c-erbB-2 and CA15-3 in saliva, where the thioygylcolic acid forms a self-assembled monolayer on the gold surfaces. Upon binding of the immobilized antibody to an antigen, the gate potential of the HEMT changes, resulting in a change in current of the HEMT at fixed bias voltage. This change in current allows identification and, preferably, quantification of the amount of the target molecule, for example a cancer biomarker, in the sample.

One embodiment of the invention is a portable or hand-held saliva based breast cancer sensor. Other embodiments of the invention are sensors to analyze other bodily fluids or excretions such as breath, urine or blood. Advantages of the sensors include fast response time for results, portability and low cost. In one embodiment, a chemical sensor array can be integrated with wireless communication circuits for remote sensor applications. For example, a digital signal cancer detector can wirelessly send the testing results directly to a user's doctor.

In another embodiment of the invention, evidence of kidney injury is detected by an HEMT functionalized with thioglycolic acid coupling kidney injury molecule-1 (KIM-1) antibodies to a gold surface of the gate of the HEMT. When in the presence of KIM-1, the gate potential of the HEMT changes, resulting in a current change in the HEMT at fixed bias voltage. This change in current can be used to detect and, preferably, quantify KIM-1 biomarker present in a sample.

In yet another embodiment of the invention, the sensor is used to detect heavy metals. Heavy metal detection can involve an HEMT functionalized with a densely coated capture reagent. $Hg^{2+}$, $Cu^{+2}$ and $Pb^{2+}$ detection can be achieved according to the invention. One embodiment is a method in which chelating agents remove heavy metal ions from a sample, where chelating ligands and metal ions bind to form metal complexes, normally called "chelation." A strong chelating agent is dimercaprol (BAL), which contains two thiol groups capable of reacting with arsenic, lead and mercury. Other widely used chelating agents include diaminoethanetetraacetic acid (EDTA), 2,3-bis-sulfanylbutanedioic acid (DMSA), and 2,3-dimercapto-1-propanesulfonic acid (DMPS). FIGS. 1A-1D show the chemical structures for BAL, EDTA, DMSA, and DMPS, respectively.

In one embodiment of the invention, $Hg^{2+}$, $Cu^{+2}$ or $Pb^{2+}$ is detected when chelating agents used as the capture reagent immobilize the metal on the HEMT surface. The surface of AlGaN can have a thin layer (~5 nm) of gold between the AlGaN surface and the chelating agent. Gold permits deposition of any chelating agent comprising a thiol group on the surface through Au—S bonding. The thiol, amine, and carboxyl groups of the bound chelating agents bind heavy metal ions to the surface of the HEMT.

Figure 2:
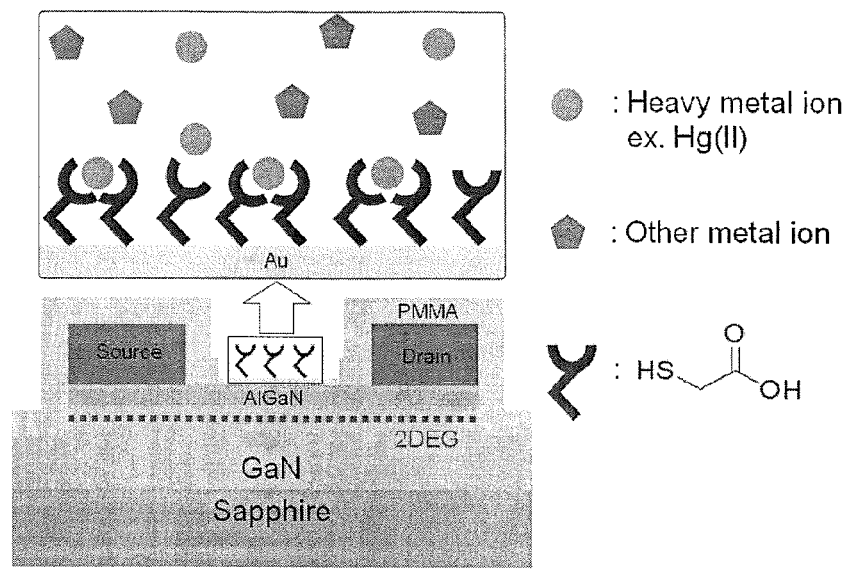
FIG. 2 shows a schematic representation of an exemplary embodiment of an AlGaN/GaN HEMT sensor of the present disclosure.

FIG. 2 shows a schematic of an exemplary embodiment of an AlGaN/GaN HEMT sensor according to an embodiment of the invention. The functionalization is an Au-coated gate area with thioglycolic acid, $HSCH_2COOH$, for Hg(II) detection. A self assembled monolayer of thioglycolic acid molecules is adsorbed onto the gold gate by a S—Au bond between the gold surface and thiol-group. The immobilized carboxyl groups function as capture reagents to capture $Hg^{2+}$, $Cu^{+2}$, and/or $Pb^{2+}$ ions. Alternative binding groups that can function as capture reagents are derived, for example, from cysteamine ($NH_2CH_2CH_2SH$) or 1,2-ethanedithiol ($HSCH_2CH_2SH$).

In one embodiment, the gold-gated region is functionalized with chelating agents immobilized on the HEMT surface, such as BAL, EDTA, DMSA, and DMPS. One portion of the chelating agent binds to the Au surface and the other portion functions as a capture reagent of heavy metals by chelating with heavy metals, such as $Hg^{2+}$, $Cu^{+2}$, or $Pb^{2+}$. The charge of the metal ions affects the gate potential of HEMTs. The change in current in the HEMT at fixed bias voltage allows detection and, preferably, quantification of the amount of the heavy metal ions in a sample.

In one embodiment, the device is a portable or hand-held trace heavy-metal sensor for environmental and health related applications. The sensor can detect heavy metals in aqueous solution including breath condensate, urine or blood. Advantages of the sensing device include fast response time, portability and low cost. In one embodiment, a heavy metal detector can be used as a wireless based sensor to transmit a digital signal of the test results directly to a recipient.

Another embodiment of the invention is a pH meter for fluids such as breath, saliva, urine or blood. Gates of HEMTs can be functionalized with noble metal oxides for detecting proton and hydroxide ions. In one embodiment, a $Sc_2O_3$ gate dielectric is formed on AlGaN/GaN HEMTs to provide high sensitivity for detecting changes in pH of electrolyte solutions. HEMTs with $Sc_2O_3$ exhibit a linear change in current of 37 μA/pH between a pH range of 3 to 10. The HEMT pH sensors are stable with a resolution of <0.1 pH over the entire pH range. The HEMTs can be used to monitor solution pH changes between 7 and 8, a range of interest for testing human blood.

Figure 3A:
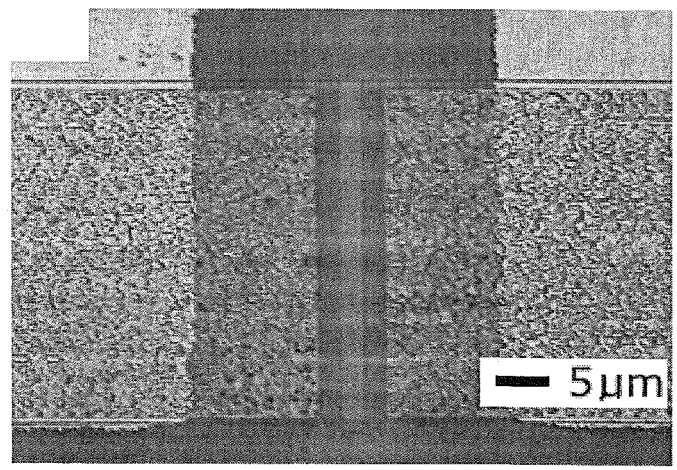
FIG. 3A shows a scanning electron microscope (SEM) image of an exemplary gateless HEMT.
Figure 3B:
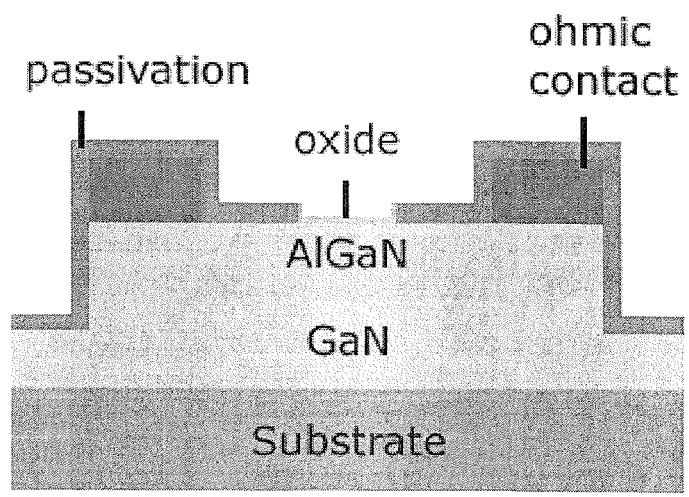
FIG. 3B shows a schematic representation of an exemplary HEMT with a non-native oxide as a gate dielectric layer.
Figure 4A:
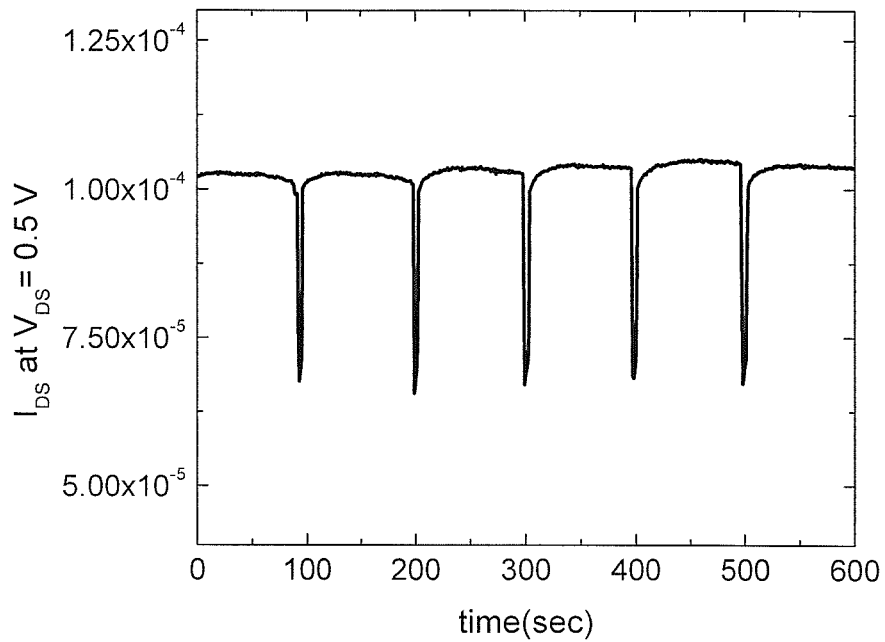
FIG. 4A is a plot showing the effects of EBC exposure, in the form of multiple exhaled breaths (each breath <1 sec), on the current change.
Figure 4B:
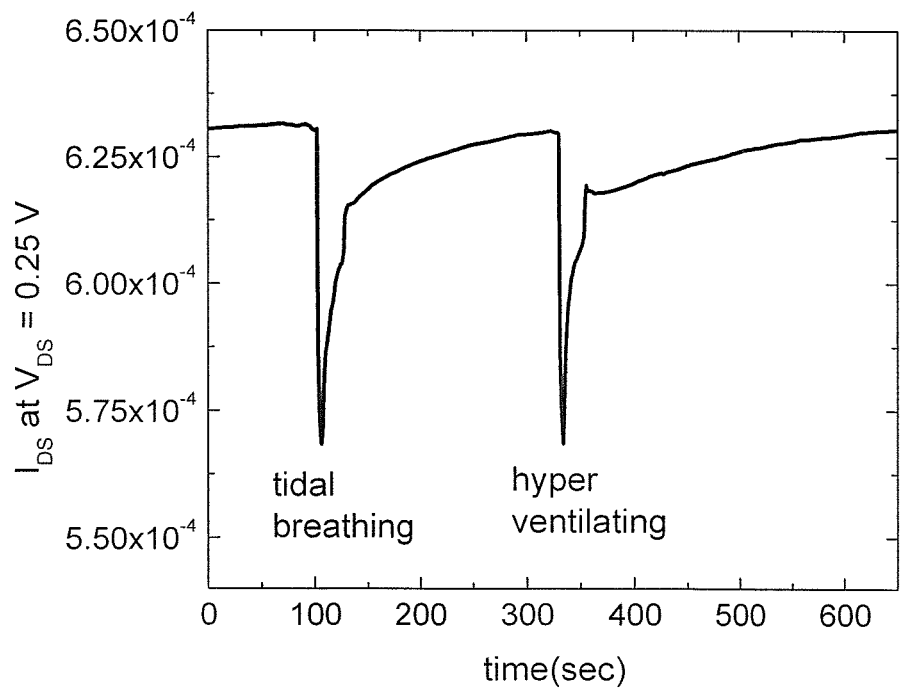
FIG. 4B is a plot showing the effects of ventilation strength on the HEMT current.

FIG. 3A shows a scanning electron microscope (SEM) image of a HEMT with a gate dielectric layer. FIG. 3B shows a schematic diagram of a HEMT with a gate dielectric layer (labeled as oxide). FIG. 4A shows the effects of EBC exposure, in the form of multiple exhaled breaths (where each breath <1 second), on the current. FIG. 4B shows the effects of ventilation strength on the HEMT current, where the duration of the breath is 5 seconds.

In other embodiments of the invention, a nanorod gated AlGaN/GaN HEMT is a detector for glucose. The nanorod arrays can be selectively grown on the gate area to immobilize glucose oxidase (GOx). The nanorods can be, for example, metal oxide and/or nitride based nanorods. Nanorod metal oxides include, but are not limited to, SnO, $TiO_2$, GaN, MgO, ZnMgO, and $In_2O_3$ nanorods. For example, one-dimensional ZnO nanorods on the gate area result in a very high specific surface area with high surface to volume ratio and provide favorable micro-environments for the immobilization of GOx.

The AlGaN/GaN HEMT drain-source current has a rapid response, of less than 5 seconds, when glucose in a buffer with a pH value of 7.4 is added to the GOx immobilized ZnO nanorods surface. A wide range of glucose concentrations from to 0.5 nM to 125 μM can be detected. For example one sensor according to an embodiment of the invention exhibited a linear range from 0.5 nM to 14.5 μM with a limit of detection of 0.5 nM.

Following are examples that illustrate embodiments of the invention. These examples should not be construed as limiting. All percentages are by weight and all solvent mixture proportions are by volume unless otherwise noted.

Example 1

Selective Detection of Hg(II) ions from Cu(II) and Pb(II)

$Hg^{2+}$ and $Cu^{2+}$ ions are easily detected with sensors fabricated with Au-gated and thioglycolic acid functionalized Au-gated GaN/AlGaN HEMTs.

The HEMT structures consisted of a 2 μm thick undoped GaN buffer and 250 Å thick undoped $Al_{0.25}Ga_{0.75}N$ cap layer. The epi-layers were grown by molecular beam epitaxy system on 2" sapphire substrates at SVT Associates. Mesa isolation was performed with an Inductively Coupled Plasma (ICP) etching with $Cl_2$/Ar based discharges at −90 V dc self-bias, ICP power of 300 W at 2 MHz, and a process pressure of 5 mTorr. Ohmic contacts of 50×50 μm² separated with gaps of 10, 20, and 50 μm were formed by e-beam deposition of Ti/Al/Pt/Au patterns by lift-off and annealed at 850° C. for 45 sec under flowing $N_2$ for source and drain metal contacts. A 5-nm thin gold film was deposited as the gate metal for two sets of sample sensors. One sensor had a bare Au-gate and the other sensor had an Au-gate that was functionalized with a self-assembled monolayer of thioglycolic acid. An increase in the hydrophilicity of the surface treated with thioglycolic acid functionalization was confirmed by contact angle measurements of a water drop of the surface of bare Au (see FIG. 5A) and thioglycolic acid functionalized Au (see FIG. 5B), which showed a change in contact angle from 58.4° to 16.2° after the surface treatment. A 500-nm-thick poly(methyl methacrylate) (PMMA) film was used to encapsulate the source/drain regions, with only the gate region exposed to allow the liquid solutions to access the bare Au-gate or functionalized Au-gate surface. The source-drain current-voltage characteristics were measured at 25° C. using an Agilent 4156C parameter analyzer with the Au-gated region exposed to different concentrations of $Hg^{2+}$, $Ca^{2+}$, $Pb^{2+}$, $Mg^{2+}$ or $Na^+$ solutions. AC measurements were performed to prevent side electrochemical reactions with modulated 500-mV bias at 11 Hz.

A schematic cross-section of the device with $Hg^{2+}$ ions bound to thioglycolic acid functionalized on the gold gate region is shown in FIG. 2. A self assembled monolayer of thioglycolic acid molecule was adsorbed onto the Au-gate due to strong interaction between gold and the thiol-group for the functionalized sensors. Excess thioglycolic acid molecules were rinsed from the monolayer using DI water. XPS and electrical measurements confirmed a high surface coverage of thioglycolic acid molecules with Au—S bonding formation on the AlGaN surface.

FIG. 6 shows the change in drain current of a bare Au-gated AlGaN/GaN HEMT sensor and a thioglycolic acid functionalized AlGaN/GaN HEMT sensor exposed to $10^{-5}$ M $Hg^{2+}$ ion solutions as compared to being exposed to DI water ($IH_2O$—$I10^{-5}$ M of $HgCl_2$). The drain current of both sensors decreased after exposure to $Hg^{2+}$ ion solutions. The drain current reduction of the thioglycolic acid functionalized AlGaN/GaN HEMT sensors exceeded that of the bare Au-gate sensor by almost 80%. Though not to be bound by theory, the mechanisms of the drain current reduction for bare Au-gate and thioglycolic acid functionalized AlGaN/GaN HEMT sensors are probably quite different. For the thioglycolic acid functionalized AlGaN/GaN HEMT, the thioglycolic acid molecules on the Au surface align with carboxylic acid functional groups extending toward the solution. The carboxylic acid functional group of the adjacent thioglycolic acid molecules can form chelates (R—COO⁻($Hg^{2+}$)⁻OOC—R) with the $Hg^{2+}$ ions. Upon chelation, one would expect the charges of trapped $Hg^{2+}$ ion in the R—COO⁻($Hg^{2+}$)⁻OOC—R to change the polarity of the thioglycolic acid molecules. Because $Hg^{2+}$ ions were used in the experiments, no Au-mercury amalgam is expected to form on the bare Au-surface.

Figure 7A:
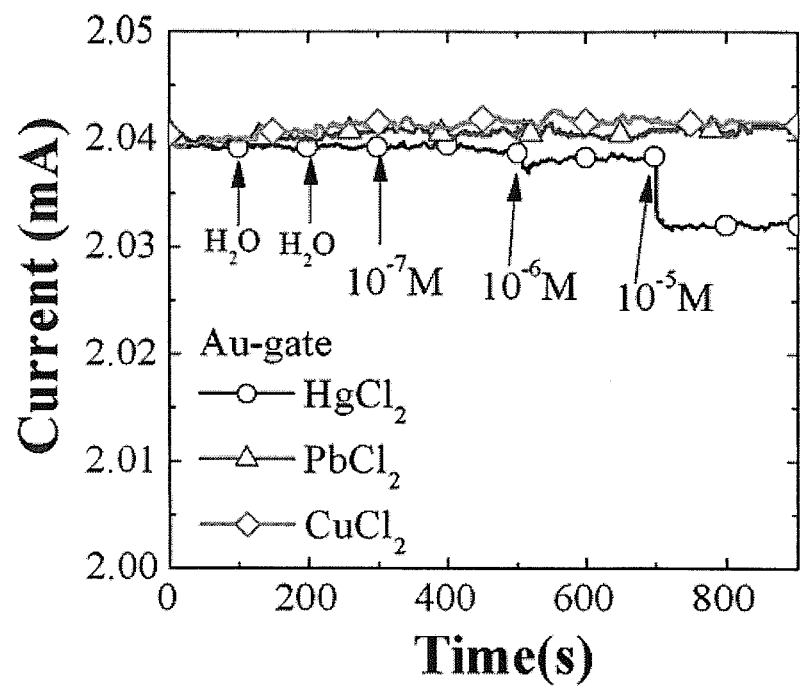
FIG. 7A shows time dependent response of the drain current as a function of $Hg^{2+}$, $Cu^{2+}$ and $Pb^{2+}$ ion concentrations for a bare Au-gate AlGaN/GaN HEMT sensor.
Figure 7B:
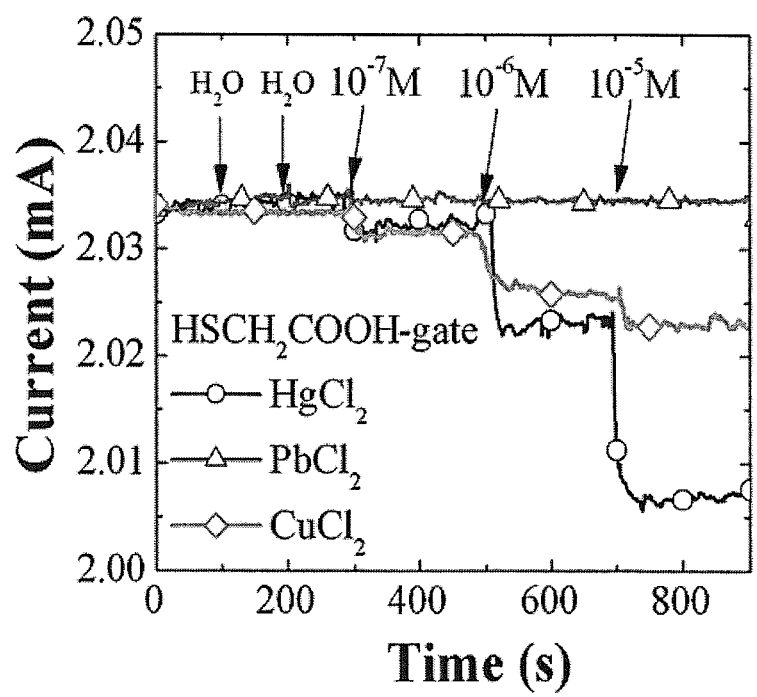
FIG. 7B shows time dependent response of the drain current as a function of $Hg^{2+}$, $Cu^{2+}$, and $Pb^{2+}$ ion concentrations for a thioglycolic acid functionalized Au-gate AlGaN/GaN HEMT sensor.

FIGS. 7A and 7B show time dependence of the drain current for the two types of sensors for detecting $Hg^{2+}$, $Cu^{2+}$, and $Pb^{2+}$ ions. Both type of sensors showed very short response time (less than 5 seconds), when exposed to $Hg^{2+}$ ion solution. The limits of detection for $Hg^{2+}$ ion detection for the bare Au-gate and thioglycolic acid functionalized sensor were $10^{-6}$ and $10^{-7}$ M, respectively. Neither sensor could detect $Pb^{2+}$ ions. For the $Cu^{2+}$ ions, the detection limit of the thioglycolic acid functionalized sensor was around $10^{-7}$ M, while the bare Au-gate could not detect the $Cu^{2+}$ ions as shown in FIG. 7.

Figure 8A:
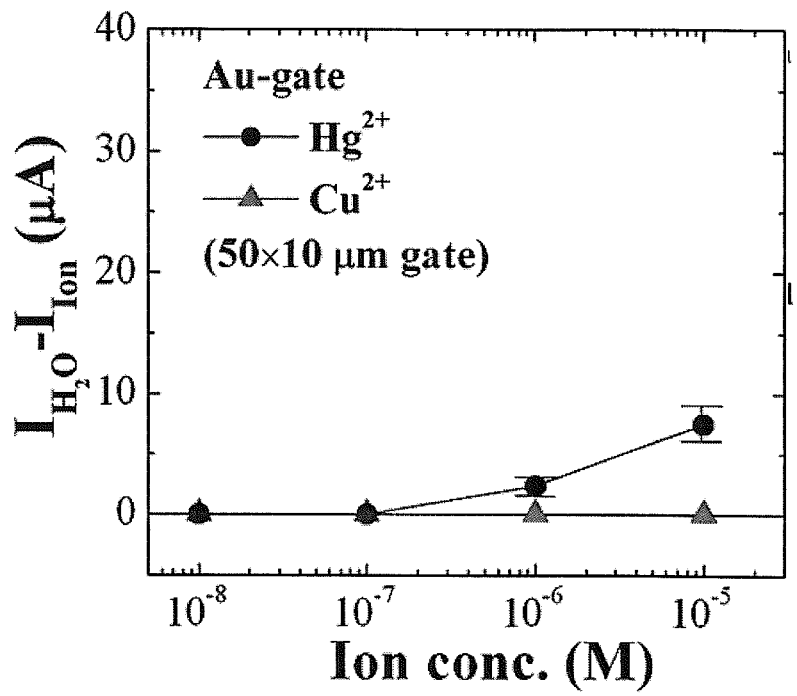
FIG. 8A shows drain current changes in response to $Hg^{2+}$ and $Cu^{2+}$ ions as a function of the ion concentration for the bare Au-gate AlGaN/GaN HEMT sensor.
Figure 8B:
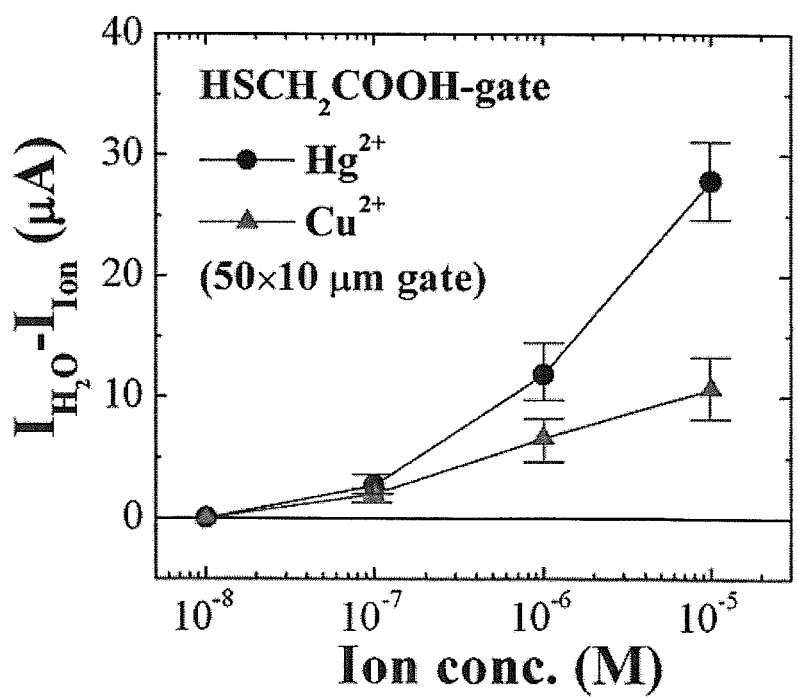
FIG. 8B shows drain current changes in response to $Hg^{2+}$ and $Cu^{2+}$ ions as a function of the ion concentration for the thioglycolic acid functionalized Au-gate AlGaN/GaN HEMT sensor.
Figure 9:
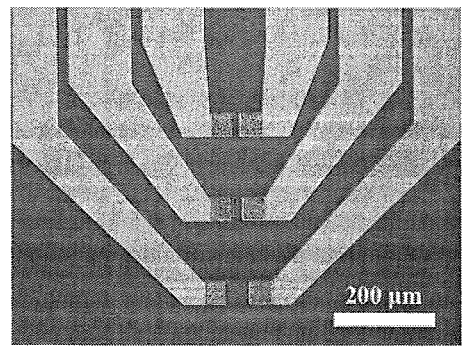
FIG. 9 shows a plan view photograph of a multiple cell AlGaN/GaN HEMT sensor.
Figure 10:
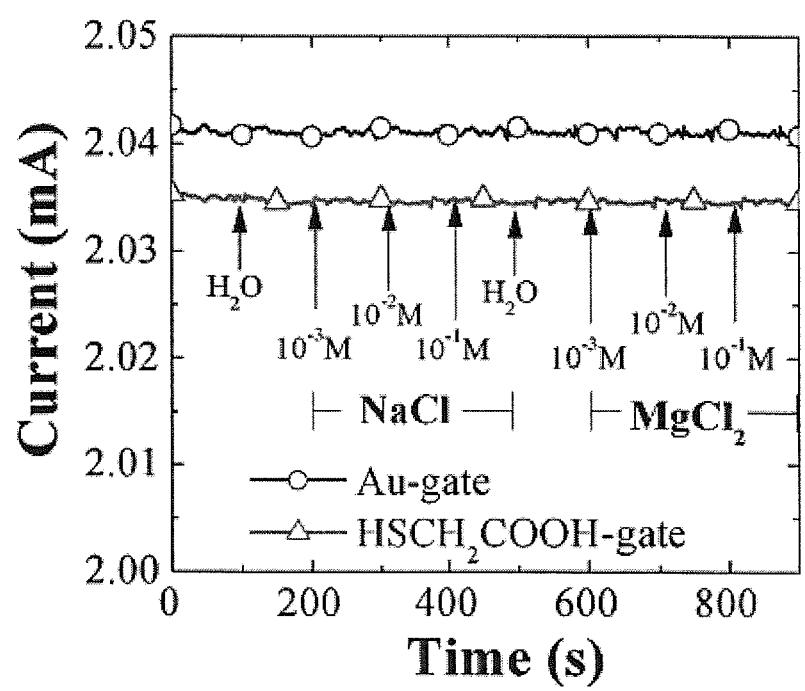
FIG. 10 shows time dependent change in the drain current in response to $Na^+$ and $Mg^{2+}$ with a bare Au-gated HEMT and a thioglycolic acid functionalized Au-gated HEMT sensor of the invention.

FIGS. 8A and 8B show the drain current changes in response to $Hg^{2+}$ and $Cu^{2+}$ ions as a function of the ion concentration for the two different surfaces. The difference in the response between the bare Au-gate and the thioglycolic acid functionalized sensor offers the possibility for selective detection for $Hg^{2+}$ and $Cu^{2+}$ ions presented in a single solution with a sensor chip containing both types of sensors, as shown in FIG. 9. The dimension of the active area of the AlGaN/GaN HEMT sensor is less than 50 μm×50 μm, and the sensors can be fabricated as an array of individual sensors. The fabrication of both sensors is identical except for the thioglycolic acid functionalized sensor, which has an additional functionalization step. This step can be accomplished with a micro-inkjet system to locally functionalize surfaces. The bare Au-gate and thioglycolic acid functionalized sensors also showed excellent sensing selectivity (over 100 times higher selectivity) over $Na^+$ and $Mg^{2+}$ ions. As illustrated in FIG. 10, there was almost no detection of $Na^+$ and $Mg^{2+}$ ions for both types of sensors with 0.1 M concentrations.

Figure 11A:
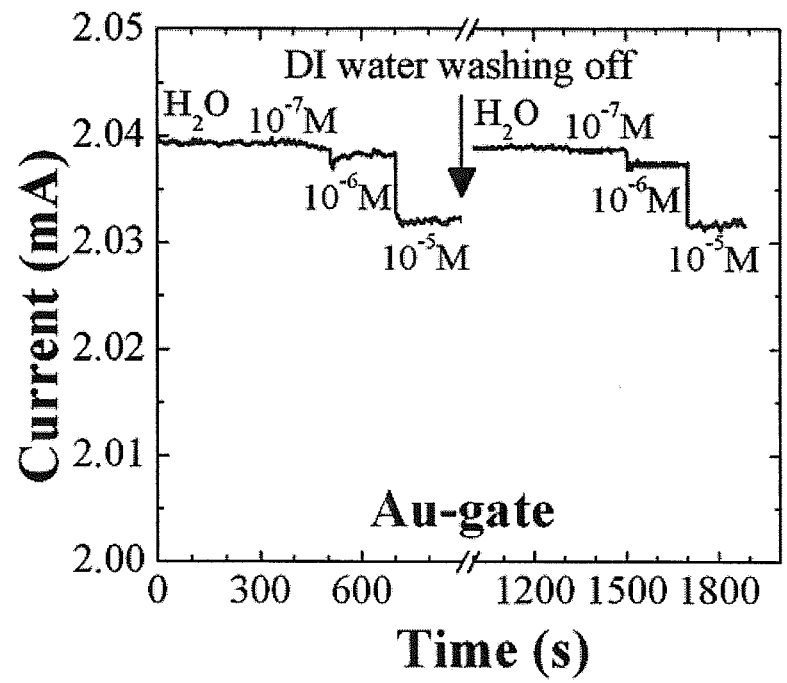
FIG. 11A shows recyclability for the bare Au-gate.
Figure 11B:
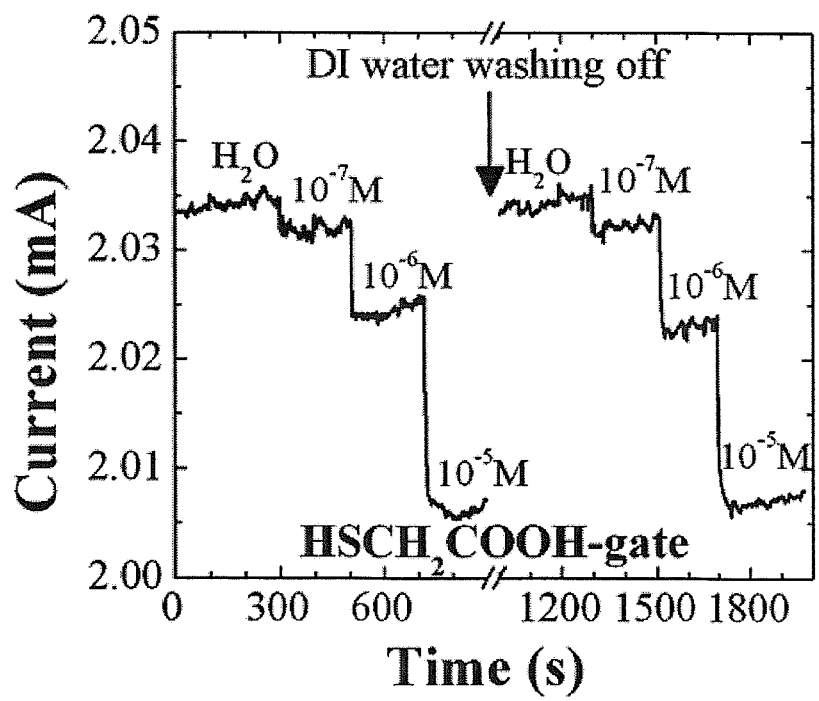
FIG. 11B shows recyclability for the thioglycolic acid functionalized Au-gate surface.

Most semiconductor based chemical sensors are not reusable. The bare Au-gate and thioglycolic acid functionalized sensors showed very good reusability, as shown in FIGS. 11A and 11B, respectively. After a simple rinse with DI water, the sensors can be reused for $Hg^{2+}$ ion detection repeatedly and the responses to different ionic solutions remain unchanged. The stability of thioglycolic acid functionalized Au surface is affected by several factors, such as oxygen level, light, and initial packing quality. The subject devices were stored in nitrogen ambient and repeatedly used over a couple of weeks without substantial diminishment of efficacy.

The $Hg^{2+}/Ca^{2+}$ sensor can operate at 0.5 V of drain voltage and 2 mA of drain current. However, the operation voltage and device size can be further reduced to minimize the power consumption to μW range. The sensor can be integrated with a commercially available hand-held wireless transmitter to realize a portable, fast response and high sensitivity $Hg^{2+}$ and $Cu^{2+}$ ion detector.

In summary, bared Au-gate and thioglycolic acid functionalized AlGaN/GaN HEMT sensors have demonstrable ability to detect heavy ions. The bare Au-gate sensor was sensitive to $Hg^{2+}$, and thioglycolic acid functionalized sensors could detect both $Hg^{2+}$ and $Cu^{2+}$ ions. By fabricating an array of the sensors on a single chip and selectively functionalizing some sensors with thioglycolic acid, a multi-functional specific detector can be fabricated. Such a sensor array can be used to quantitatively detect $Hg^{2+}$ ions in $Cu^{2+}$ ion solution or $Cu^{2+}$ ions in $Hg^{2+}$ ion solution. Both bare Au-gate and thioglycolic acid functionalized sensors can be repeatedly used after a simple DI water rinse.

Example 2

Detection of Prostate Specific Antigen

Functionalized of Au-gated AlGaN/GaN HEMTs of the invention were used to detect prostate specific antigen (PSA). The PSA was specifically recognized through PSA antibody, anchored to the gate area in the form of carboxylate succinimidyl ester. A wide range of concentrations from to 1 μg/ml to 10 pg/ml of PSA was investigated, which is lower than the cut-off value of 2.5 ng/ml that is used as an indication for the need of biopsy.

The HEMT structures consisted of a 3 μm thick undoped GaN buffer, a 30 Å thick $Al_{0.3}Ga_{0.7}N$ spacer, and a 220 Å thick Si-doped $Al_{0.3}Ga_{0.7}N$ cap layer. Epi-layers were grown by rf plasma-assisted Molecular Beam Epitaxy on the thick GaN buffers produced on sapphire substrates by metal organic chemical vapor deposition (MOCVD). Mesa isolation was performed with an Inductively Coupled Plasma (ICP) etching with $Cl_2$/Ar based discharges at −90 V dc self-bias, ICP power of 300 W at 2 MHz, and a process pressure of 5 mTorr. 10×50 μm² Ohmic contacts separated with gaps of 5 μm were formed by e-beam deposited Ti/Al/Pt/Au patterned by lift-off and annealed at 850° C. for 45 sec under flowing $N_2$. Poly(methyl methacrylate) (PMMA) was used to form 400-nm-thick layer encapsulating the source/drain regions, with only the gate region exposed to allow the liquid solutions to contact the gate surface. The source-drain current-voltage characteristics were measured at 25° C. using an Agilent 4156C parameter analyzer with the gate region exposed to solution. AC measurements were performed with modulated 500-mV bias at 11 Hz to prevent side electrochemical reactions.

Figure 12A:
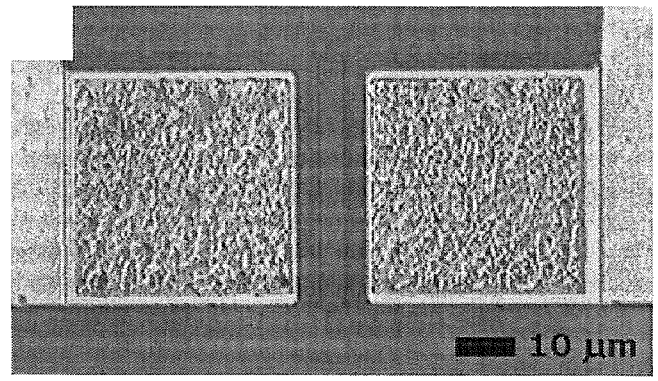
FIG. 12A shows a plan view photomicrograph of a completed HEMT device of the invention with a 5-nm Au film in the gate region.
Figure 12B:
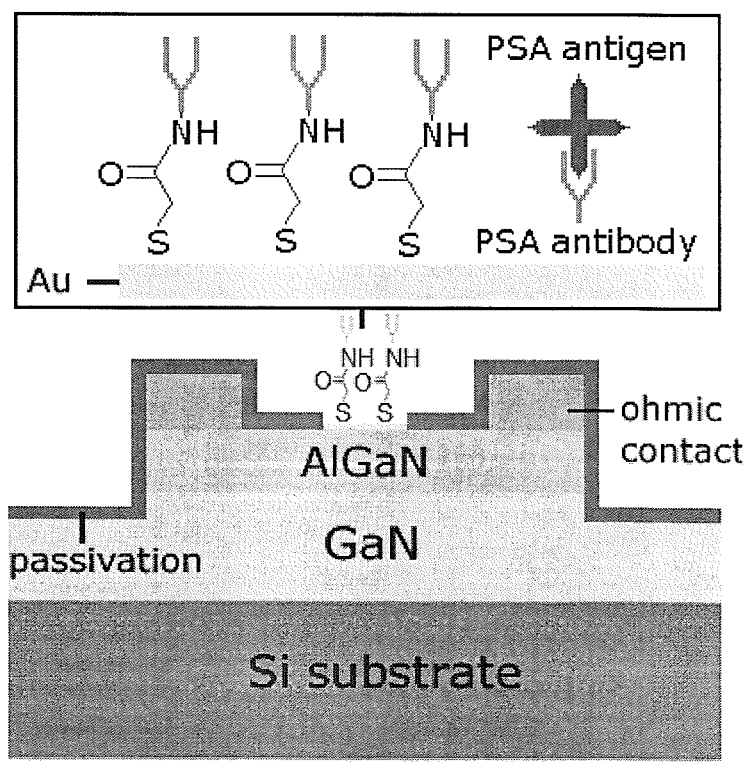
FIG. 12B shows a schematic of an AlGaN/GaN HEMT of the invention, where the Au-coated gate area was functionalized with PSA antibody on thioglycolic acid.

A plan view photomicrograph of a completed device is shown in FIG. 12A and a schematic cross-section of the device is shown in FIG. 12B. The Au surface was functionalized with a specific bifunctional molecule. Here, thioglycolic acid, $HSCH_2COOH$, was attached to the Au surface in the gate area as a self assembled monolayer adsorbed on the gold gate.

The devices were first placed in the ozone/UV chamber for 3 minutes and then submerged in a 1 mM aqueous solution of thioglycolic acid for 24 hours at room temperature, resulting in binding of the thioglycolic acid to the Au surface in the gate area with the COOH groups available for further chemical functionalization. XPS and electrical measurements were taken to confirm a high surface coverage and Au—S bonding formation on the surface. The device was freshly cleaned with deionized water to remove unlinked thioglycolic acids. The carboxylic acid functional groups were activated by submerging the device in a 0.1 mM solution of N,N'-dicyclohexylcarbodiimide (DCC) in dry acetonitrile for 30 minutes and then in a 0.1 mM solution of N-hydroxysuccinimide in dry acetonitrile for 1 hour. These functionalization steps resulted in the formation of succinimidyl ester groups on the gate area of AlGaN/GaN HEMT, as shown in FIG. 12B. The device was incubated in a phosphate buffered saline (PBS) solution of anti-PSA monoclonal antibody for 18 hours before real time measurement of PSA.

Figure 13A:
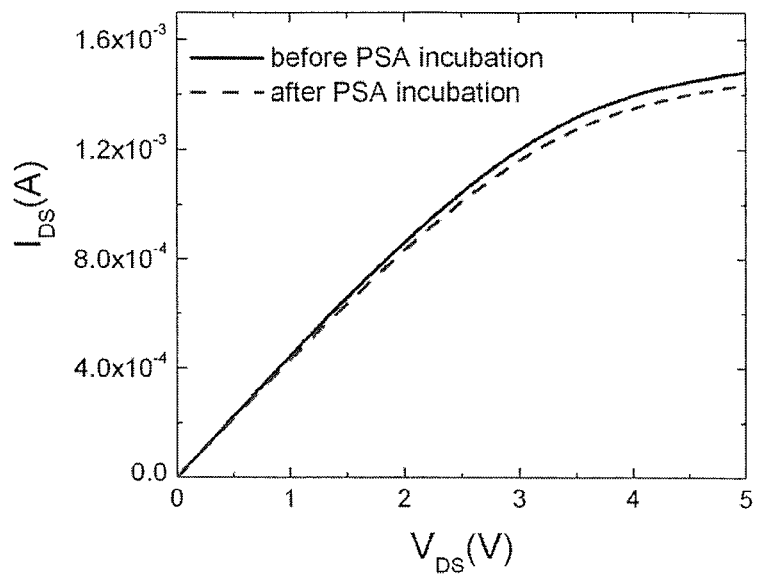
FIG. 13A shows I-V characteristics of an AlGaN/GaN HEMT sensor of the invention before and after PSA incubation.

After incubation in a PBS buffered solution containing PSA at a concentration of 1 μg/ml, the device surface was thoroughly rinsed with deionized water and dried with a nitrogen stream. The electrical properties of the devices, source and drain current, were measured before and after PSA incubation as shown in FIG. 13A. As previously described, the electrons in 2DEG channel of the AlGaN/GaN HEMT are induced by piezoelectric and spontaneous polarization effects. Positive counter-charges at the AlGaN surface layer are induced by the 2DEG. Any slight changes in the ambient environment of the AlGaN/GaN HEMT affect the surface charges of the AlGaN/GaN HEMT. These changes in the surface charge are transduced into a change in the concentration of the 2DEG in the AlGaN/GaN HEMTs, leading to the slight decrease in the conductance for the device after PSA incubation.

Figure 13B:
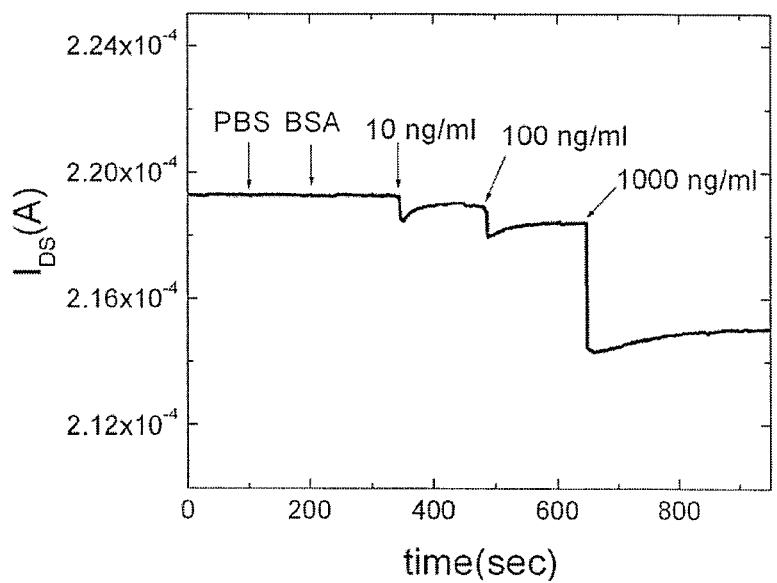
FIG. 13B shows drain current over time for PSA when sequentially exposed to PBS, BSA, and PSA when using an AlGaN/GaN HEMT sensor of the invention.

FIG. 13B shows the real time PSA detection in PBS buffer solution using change in the source-to-drain current with a constant bias of 500 mV. No current change can be seen with the addition of buffer solution around 100 sec and the addition of nonspecific bovine serum albumin (BSA) around 200 sec, showing relatively high stability of the device and chemical surface modification. In clear contrast, the current change showed a rapid response of less than 5 seconds when 10 ng/ml PSA was introduced to the antibody on the surface. The abrupt current change, mainly due to the exposure of PSA in a buffer solution, stabilized after the PSA thoroughly diffused into the buffer solution.

Further real-time testing for the detection limit of PSA of less dilute concentrations was carried out as shown in FIG.

Figure 14A:
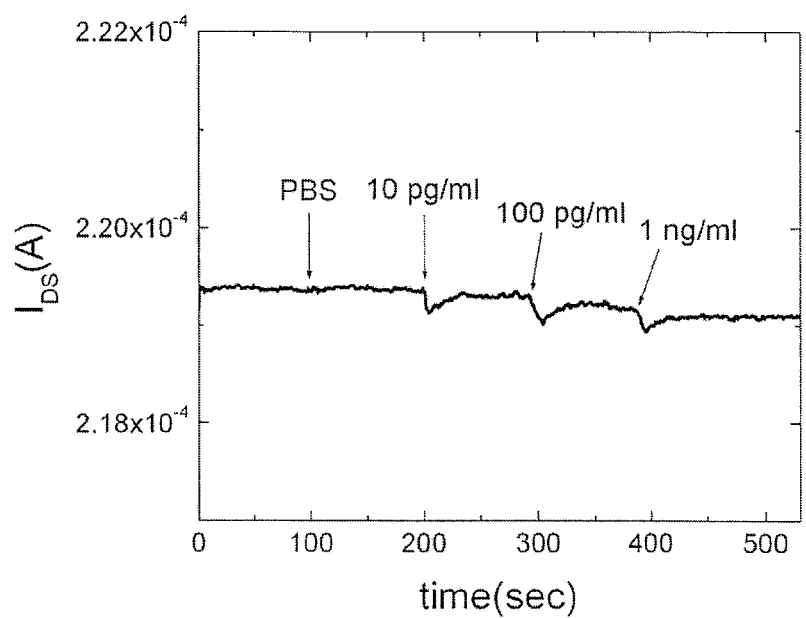
FIG. 14A shows drain current over time for PSA from 10 pg/ml to 1 ng/ml when using an AlGaN/GaN HEMT sensor of the invention.
Figure 14B:
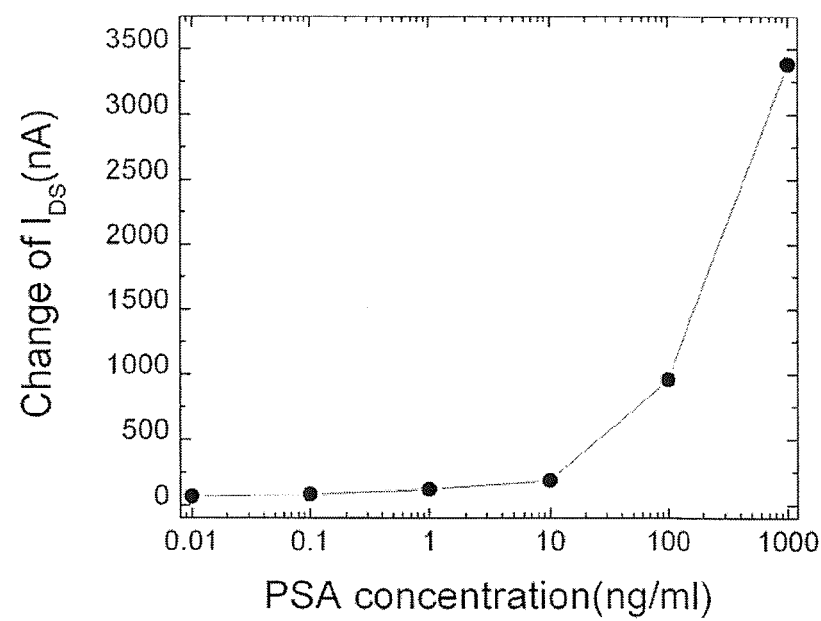
FIG. 14B illustrate change of source and drain current versus different concentrations from 10 pg/ml to 1 μg/ml of PSA using an AlGaN/GaN HEMT sensor of the invention.

14A. Three different concentrations of the exposed target PSA in a buffer solution were observed from 10 pg/ml to 1 ng/ml. The amplitude of current change for the device exposed to PSA in a buffer solution was about 3%, as illustrated in FIG. 14B. The clear current decrease of 64 nA as 10 pg/ml of PSA also indicated that the detection limit could be lowered up to several pg/ml, showing the promise of a portable electronic biological sensor for PSA screening.

As demonstrated herein, through a chemical modification sequence, the Au-gated region of an AlGaN/GaN HEMT structure can be functionalized for the detection of PSA with a sensitivity of 10 pg/ml in a buffer at clinical concentration. This electronic detection of biomolecules can occur with a compact sensor chip, which can be integrated with a commercially available hand-held wireless transmitter to realize a portable, fast and high-sensitivity prostate cancer detector.

Example 3

Detection of Changes in pH in Electrolyte Solutions

A $Sc_2O_3$ gate dielectric on AlGaN/GaN HEMTs is shown to provide high sensitivity for detecting changes in pH of electrolyte solutions, and is superior to the use of native oxide in the gate region.

The HEMT structures consisted of a 2 μm thick undoped GaN buffer and 250 Å thick undoped $Al_{0.25}Ga_{0.75}N$ cap layer. The epi-layers were grown by Metal-Organic Chemical Vapor Deposition on 100 mm (111) Si substrates at Nitronex Corporation. The sheet carrier concentration was $\sim 1\times10^{13}$ $cm^{-2}$ with a mobility of 980 $cm^2$/V-s at room temperature. Mesa isolation was achieved by using an ICP system with $Ar/Cl_2$ based discharges. Ohmic contacts of 50×50 μm$^2$ separated with gaps of 10, 20, and 50 μm were formed by lift-off of e-beam deposited Ti (200 Å)/Al (800 Å)/Pt (400 Å)/Au (800 Å). The contacts were annealed at 850° C. for 45 sec under a flowing $N_2$ ambient in a Heatpulse 610T system. A 100 Å $Sc_2O_3$ layer was deposited as a gate dielectric through a contact window of $SiN_x$ layer. Before oxide deposition, the wafer was exposed to ozone for 25 minutes, and heated in-situ at 300° C. for 10 minutes inside the growth chamber. The $Sc_2O_3$ was deposited by rf plasma-activated MBE at 100° C. using elemental Sc evaporated from a standard effusion cell at 1130° C. and $O_2$ derived from an Oxford RF plasma source.

For comparison, devices with only the native oxide present in the gate region and devices with the UV ozone-induced oxide were fabricated. FIG. 3A shows a scanning electron microscopy (SEM) image and FIG. 3B shows a cross-sectional schematic of the completed device. The gate dimension of the device is 2×150 μm$^2$. The pH solution was applied using a syringe autopipette (2-20 μl).

Prior to the pH measurements, pH 4, 7, and 10 buffer solutions from Fisher Scientific were used to calibrate the electrode and the measurements at 25° C. were carried out in the dark using an Agilent 4156C parameter analyzer to avoid parasitic effects. The pH solution was made by the titration method using $HNO_3$, NaOH, and distilled water. The electrode was a conventional Acumet standard Ag/AgCl electrode.

Figure 15:
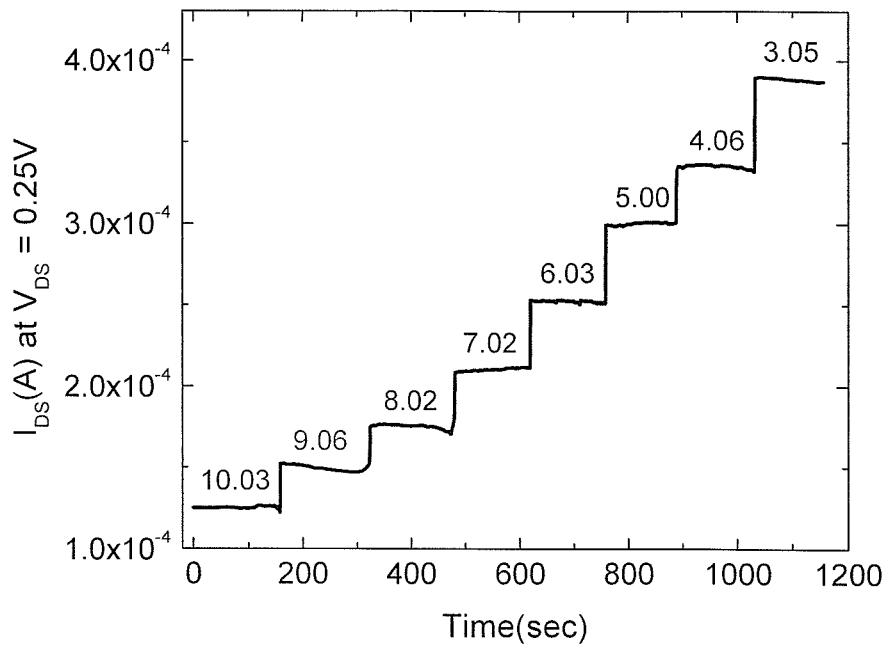
FIG. 15 shows the drain current over time using a HEMT with a gate dielectric of a non-native oxide and a fixed source-drain bias of 0.25 V for pH from 3-10.

The adsorption of aqueous solution of different pH on the surface of the HEMT affected the surface potential and device characteristics. FIG. 15 shows the current at a bias of 0.25V as a function of time from the HEMTs with $Sc_2O_3$ in the gate region exposed for 150 sec to a series of solutions whose pH was varied from 3-10. The current significantly increased as the pH was decreased upon exposure to these aqueous solutions. The change in current was 37 μA/pH. The HEMTs show stable operation with a resolution of ~0.1 pH over the entire pH range, illustrating the remarkable sensitivity of the HEMT to relatively small changes in concentration of the hydronium ion in solution. By comparison, devices with the native oxide in the gate region showed a higher sensitivity of ~70 μA/pA but a poor resolution of ~0.4 pH and showed delays in response of 10-15 seconds. The delays may result from deep traps at the interface between the semiconductor and native oxide, whose density is much higher than at the $Sc_2O_3$-nitride interface. The devices with UV-ozone oxide in the gate region did not show these incubation times for detection of pH changes and showed similar sensitivities of gate source current as the $Sc_2O_3$ gate devices (~40 μA/pH), but displayed poorer resolution (~0.25 pH). FIG. 15 shows that the HEMT sensor with $Sc_2O_3$ gate dielectric is sensitive to the concentration of the polar liquid and therefore could be used to differentiate between liquids into which a small amount of leakage of another substance has occurred.

Figure 16:
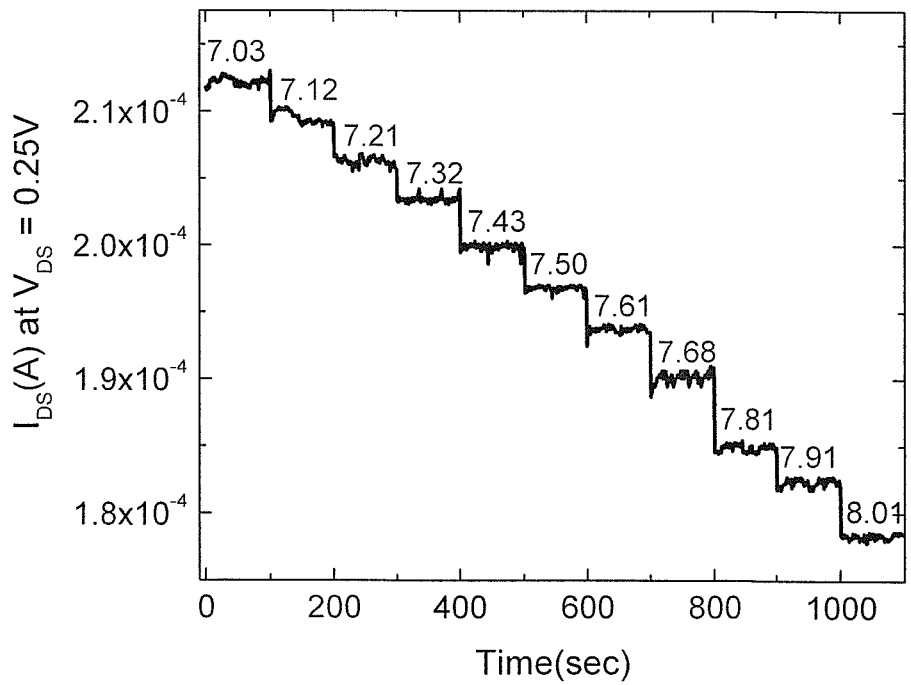
FIG. 16 shows the drain current over time using a HEMT with a gate dielectric of a non-native oxide at fixed source-drain bias of 0.25 V for pH from 7-8.

The pH range of interest for human blood is 7-8. FIG. 16 shows the change in current of the HEMTs with $Sc_2O_3$ at a bias of 0.25V for different pH values in this range. The resolution of the measurement is <0.1 pH. As previously described, the electrons in the 2DEG channel of the AlGaN/GaN HEMT are induced by piezoelectric and spontaneous polarization effects. Positive counter charges at the AlGaN surface layer are induced by the 2DEG. Any change in the ambient environment of the AlGaN/GaN HEMT affects the surface charges of the device. These changes in the surface charge are transduced into a change in the concentration of the 2DEG. Different pHs exhibit different degrees of interaction with the $Sc_2O_3$ surface. These results show that using a higher quality oxide is useful in improving pH resolution.

Example 4

Detection of Kidney Injury Molecule-1

Figure 17A:
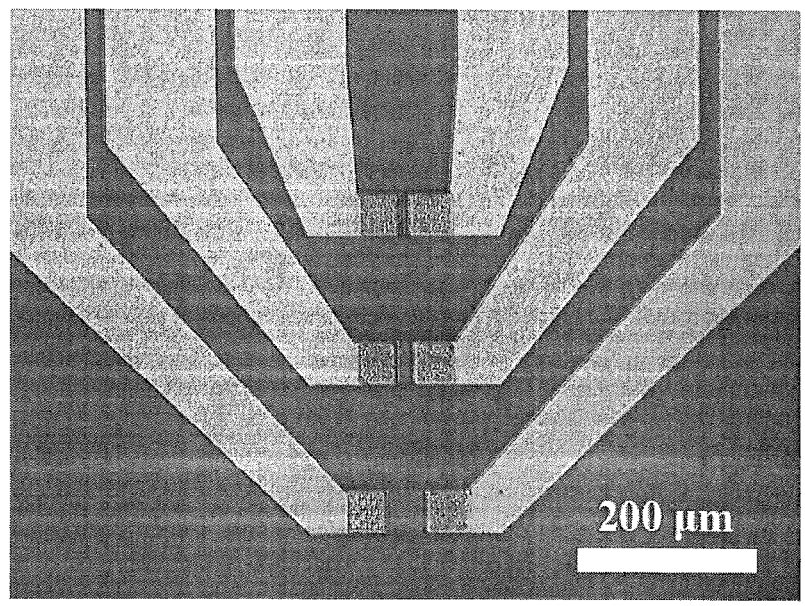
FIG. 17A shows a plan view photomicrograph of a completed device with a 5-nm Au film on the gate region.

The HEMT structure consisted of a 2 μm thick undoped GaN buffer and 250 Å thick undoped $Al_{0.25}Ga_{0.75}N$ cap layer. The epi-layers were grown by metal-organic chemical vapor deposition on 100 mm (111) Si substrates. Mesa isolation was performed with ICP etching with $Cl_2$/Ar based discharges at −90 V dc self-bias, ICP power of 300 W at 2 MHz, and a process pressure of 5 mTorr. Ohmic contacts of 50×50 μm$^2$ separated with gaps of 20 μm were formed by e-beam deposited Ti/Al/Pt/Au patterned by lift-off and annealed at 850° C. for 45 sec under a $N_2$ stream. A 5-nm thin gold film was deposited as a gate metal and functionalized as a self-assembled monolayer of thioglycolic acid. Poly(methyl methacrylate) (PMMA) was used to form a 500-nm-thick encapsulate of the source/drain regions, with the gate region exposed using e-beam lithography. A plan view photomicrograph of a completed device is shown in FIG. 17A.

Before depositing the thioglycolic acid coating, the sample was exposed to UV ozone for 5 minutes to remove surface contamination. A self-assembled monolayer of thioglycolic acid molecule was adsorbed onto the Au-gate. Excess thioglycolic acid was rinsed off with PBS buffer. An increase in the hydrophilicity of the treated thioglycolic acid functionalization surface was confirmed by contact angle measurements, which showed a change in contact angle from 58.4° to 16.2° after the surface treatment (see e.g., FIGS. 5A and 5B).

Figure 17B:
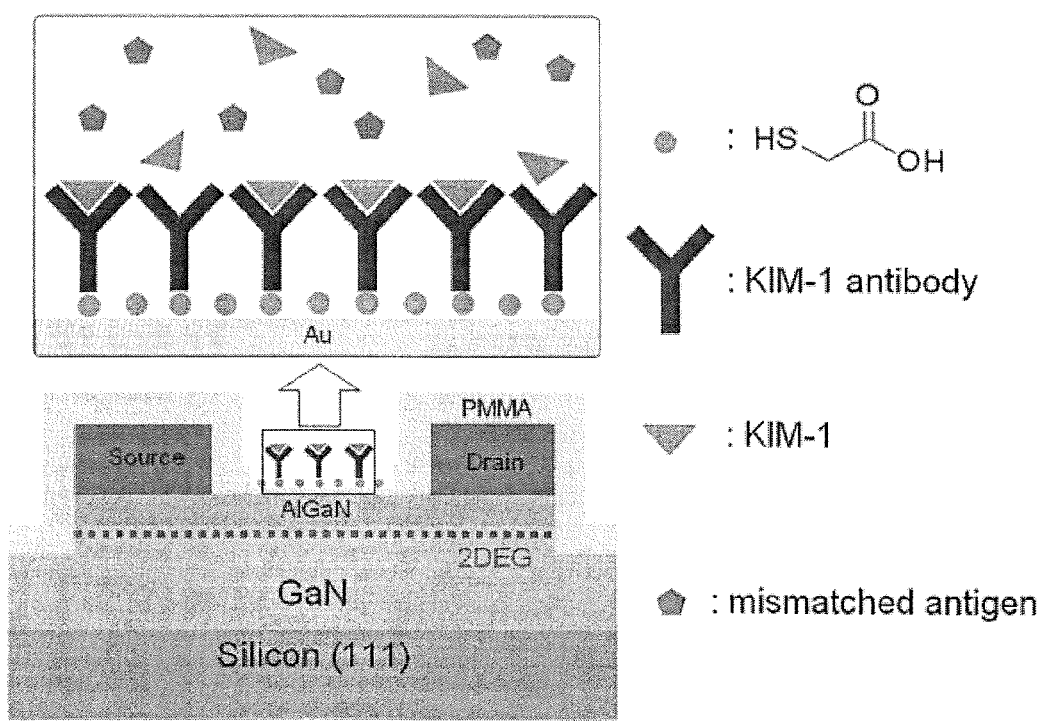
FIG. 17B shows a schematic device cross section where the Au-coated gate area was functionalized with KIM-1 antibody on thioglycolic acid.

The thioglycolic acid surface was treated with monoclonal anti-rat kidney injury molecule-1 (KIM-1) antibody in a solution of 10 mM phosphate buffer containing 4 mM sodium cyano-borohydride with pH 8.8 at room temperature for 2 hours. This antibody immobilization is based on a strong reaction between the carboxyl group on thioglycolic acid and the amine group on KIM-1 antibody. Excess KIM-1 antibodies were washed from the surface using a PBS buffer and the unreacted surface carboxyl groups were passivated by a blocking solution of 100 mM ethanolamine in 10 mM phosphate buffer with pH 8.8. FIG. 17B shows a schematic device cross-section with thioglycolic acid followed by KIM-1 antibody coating. The source-drain current-voltage characteristics were measured at 25° C. using an Agilent 4156C parameter analyzer with the KIM-1 antibody functionalized Au-gated region exposed to different concentrations of KIM-1/PBS buffer. AC measurements were performed to prevent side electrochemical reactions with modulated 500-mV bias at 11 Hz.

Figure 18:
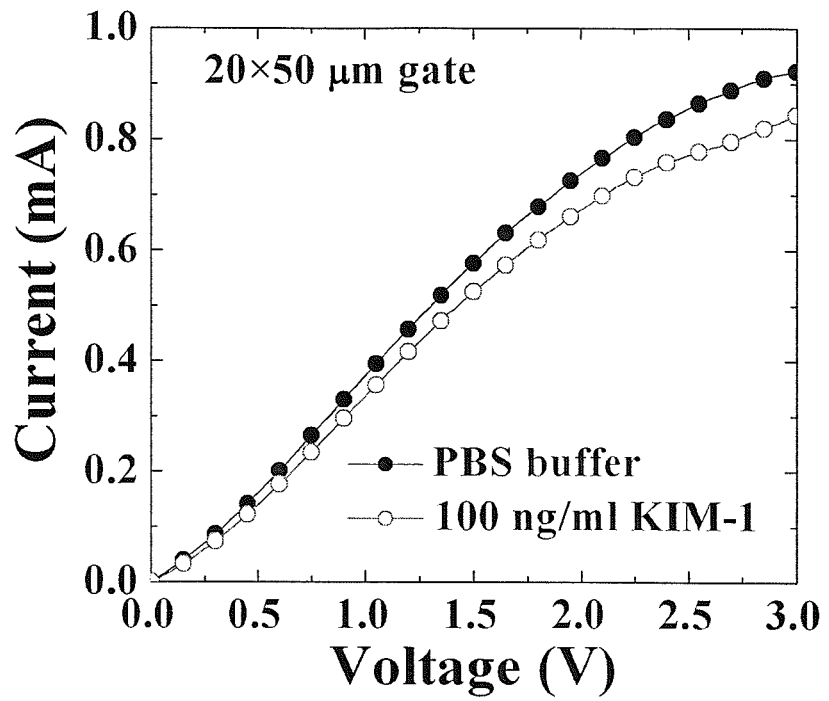
FIG. 18 shows $I_{DS}$-$V_{DS}$ characteristics of an HEMT in both PBS buffer and 100 ng/ml KIM-1.

The source-drain current($I_{DS}$) vs. voltage ($V_{DS}$) for the devices, were measured in PBS buffer and 100 ng/ml KIM-1 in PBS buffer, as shown in FIG. 18. There is a clear conductance decrease with KIM-1 exposure and this suggests that through the selective binding of KIM-1 with antibody, there are charges accumulated at the surface of the HEMT and these surface charges are transduced into a change in the carrier concentration of AlGaN/GaN 2DEG, leading to the obvious decrease in the conductance of the device after KIM-1 exposure.

Figure 19:
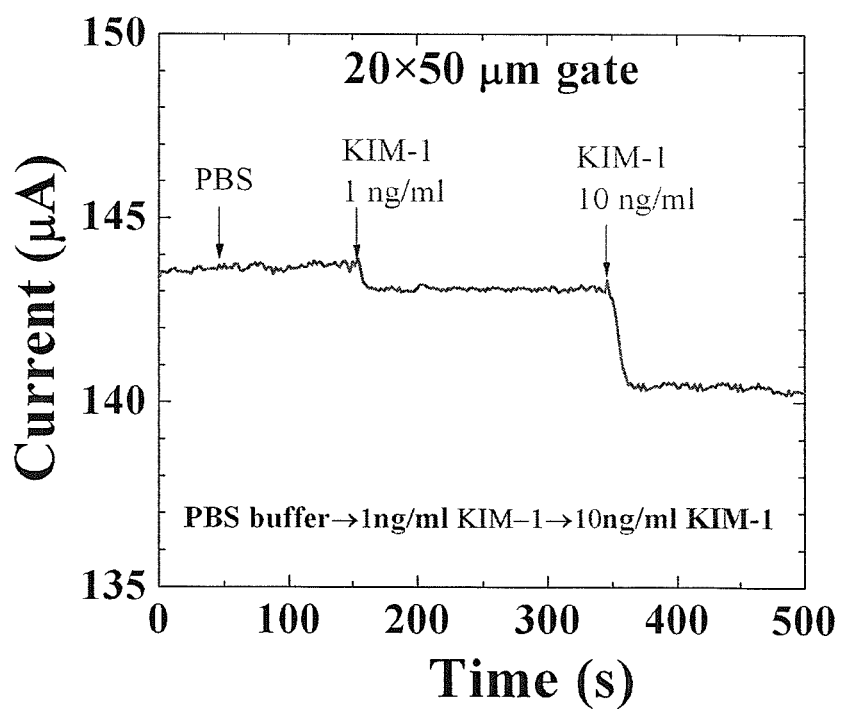
FIG. 19 shows time dependent current signal when exposing the HEMT to 1 ng/ml and 10 ng/ml KIM-1 in PBS buffer.

FIG. 19 shows the time dependent source-drain current signal with a constant bias of 500 mV for KIM-1 detection in PBS buffer solution. No current change can be seen with the addition of buffer solution around 50 sec. This stability excludes the possibility of noise due to the mechanical change of the buffer solution. By sharp contrast, the current change showed a rapid response in less than 20 seconds when 1 ng/ml KIM-1 was switched to the surface at 150 sec. The abrupt current change due to the exposure of KIM-1 in a buffer solution stabilized after the KIM-1 thoroughly mixed with the buffer. A 10 ng/ml KIM-1 solution was then applied at 350 sec, which was accompanied by a larger signal due to the higher KIM-1 concentration.

Figure 20:
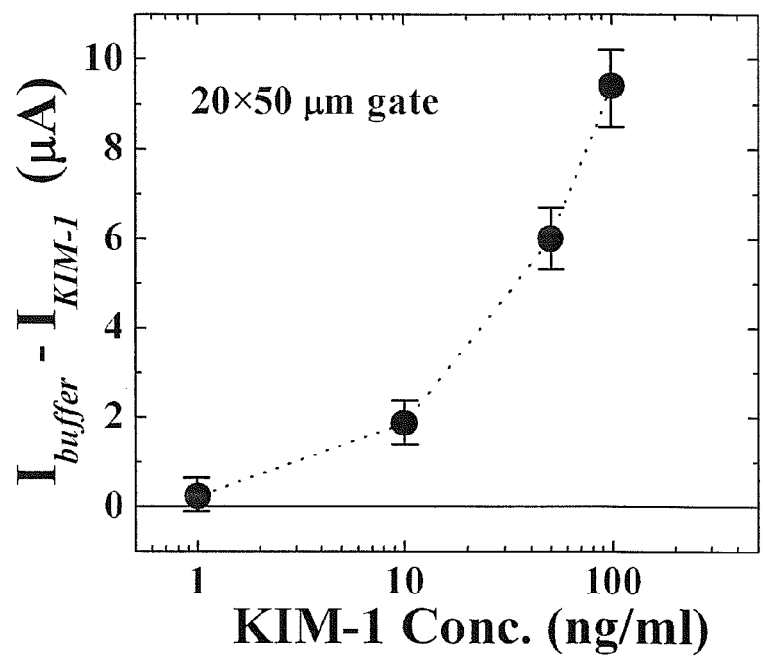
FIG. 20 shows the current change for a HEMT as a function of KIM-1 concentration.

Additional real-time tests were carried out to explore the limits of detection of KIM-1 antibody. Referring to FIG. 20, the device was exposed to 10 pg/ml, 100 pg/ml, 1 ng/ml, 10 ng/ml, and 100 ng/ml individually with each concentration repeated five times to determine the standard deviation of source-drain current response for each concentration. The limit of detection of this device was 1 ng/ml KIM-1 in PBS buffer solution and the source-drain current change is nonlinearly proportional to the KIM-1 concentration. Between each test, the device was rinsed with a wash buffer of 10 μM phosphate buffer solution containing 10 μM KCl with pH 6 to strip the antibody from the antigen. These results suggest that the HEMTs are compatible with AKI biomarker, KIM-1; are very sensitive relative to other currently available nano-devices; and are useful for preclinical and clinical applications. Similar surface modifications can be applied for detecting other important disease biomarkers and a compact disease diagnosis array can be realized for multiplex disease analysis.

Example 5

Glucose Detection

The HEMT structure consisting of a 3 μm thick undoped GaN buffer, 30 Å thick $Al_{0.3}Ga_{0.7}N$ spacer, 220 Å thick Si-doped $Al_{0.3}Ga_{0.7}N$ cap layer was provided. Epi-layers were grown by both molecular beam epitaxy and metal organic chemical vapor deposition (MOCVD) on thick GaN buffers on sapphire substrates. Mesa isolation was performed with an ICP etching with $Cl_2$/Ar based discharges at −90 V dc self-bias, ICP power of 300 W at 2 MHz, and a process pressure of 5 mTorr. 50×50 μm² Ohmic contacts separated with gaps of 10 μm were formed by e-beam deposited Ti/Al/Pt/Au patterned by lift-off and annealed at 850° C. for 45 sec under flowing $N_2$.

Figure 21:
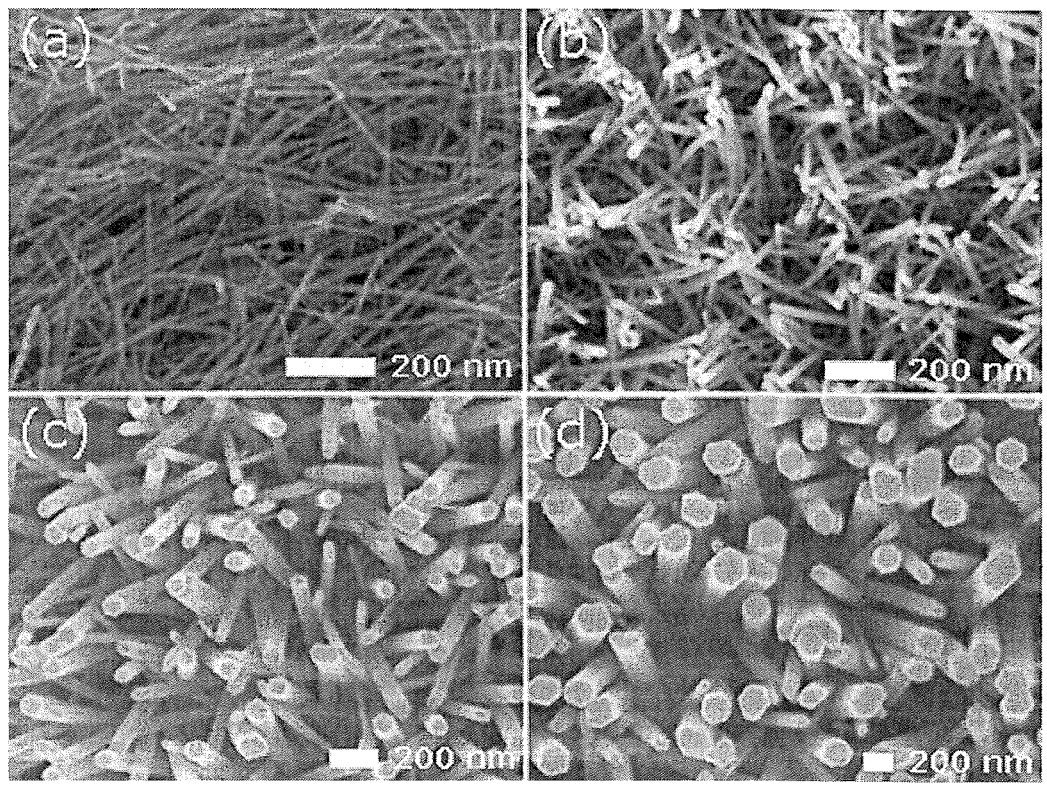
FIG. 21 shows field emission SEM images of ZnO nanorod arrays grown on the Si substrate spin-coated with different size precursors (Preparation time of ZnO nanoparticle precursors from (a) to (d): 0.5, 1, 1.5, and 2 h).

ZnO nanorods were grown in a solution of 20 mM zinc acetate hexahydrate ($Zn(NO_3)_2.6H_2O$) and 20 mM hexamethylenetriamine ($C_6H_{12}N_4$) in a flask with polypropylene autoclavable cap at a controlled temperature and pH on the HEMT substrate. Subsequently, the substrate was removed from solution, thoroughly rinsed with acetone followed by deionized water to remove any residual salts and dried in air at room temperature. The ZnO nanoparticle size was highly dependent on the nanocrystal seed preparation time. The diameters of ZnO nanorods can be carefully controlled from tens of nanometers to several hundred micrometers by the seed size used to grow the nanorods. FIG. 21 shows the effect of nanocrystal seed size on the diameters of ZnO nanorods grown on a Si (111) substrate.

Figure 22:
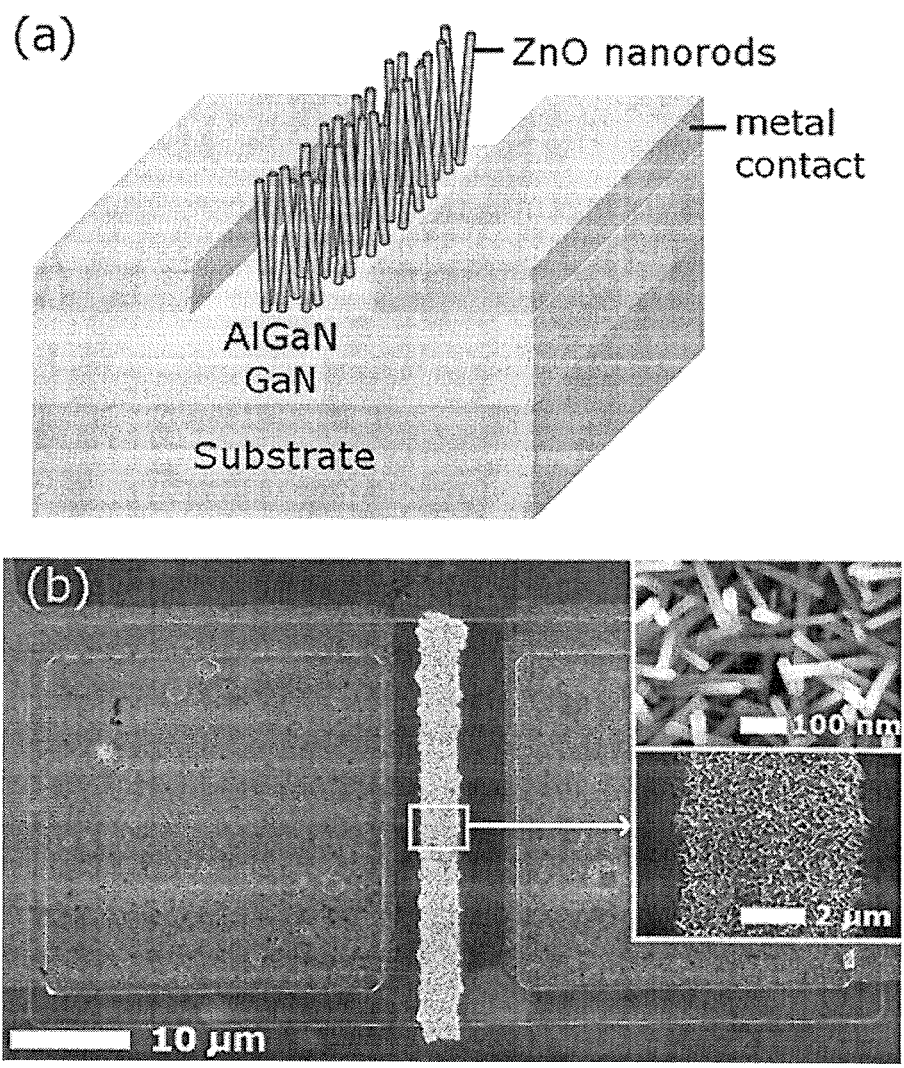
FIG. 22 shows (a) Schematic of ZnO nanorod gated AlGaN/GaN HEMT; (b) SEM image of ZnO nanorod gated AlGaN/GaN HEMT. Upper right inset shows HRTEM image of a ZnO nanorod array grown on the gate area with different scales.

By incorporating the nanorods on the HEMT gate sensing area, the total sensing area increases significantly as shown in FIG. 22(a). The conventional AlGaN/GaN HEMT detects the ambient changes through the "gate sensing area". This area is defined as gate length×gate width in the regular HEMT. Although, the gate width can be increased in order to gain higher drain current from the transistor, the sensor detection sensitivity will be the same for the HEMT having both short and longer gate width. This is due to the signal and background current proportionally increasing at the same time. The other dimension of the gate is the gate length. However, increasing the gate length increases the parasitic resistance of the HEMT and the drain current decreases. Thus, the detection sensitivity goes down. Therefore, the only way to increase the sensitivity with the same "gate dimension" is to grow 3D structures on the gate sensing area to increase the total sensing area with the area expansion to the third dimension.

FIG. 22(b) shows SEM pictures of ZnO nanorods grown on the AlGaN/GaN HEMT gate sensing area. The upper right inset in FIG. 22(b) shows a closer view of ZnO nanorod arrays grown on the gate area with different scales. The ZnO nanorods matrix provides a microenvironment for immobilizing negatively charged GOx while retaining its bioactivity, and passes charges produce during the GOx and glucose interaction to the AlGaN/GaN HEMT.

A GOx solution was prepared with a concentration of 10 mg/mL in the 10 mM phosphate buffer saline (pH value of 7.4, Sigma Aldrich). After fabricating the device, 5 μl GOx (~100 units/mg, Sigma Aldrich) solution was dropped on the surface of HEMT device. The HEMT device was kept at 4° C. in the solution for 48 hours for GOx immobilization on the ZnO nanorod arrays followed by an extensive washing to remove the unimmobilized GOx. The HEMT device was kept in the incubator for 30 minutes to make the enzyme active around 37° C.

The target glucose was applied on the device through a syringe autopipette (2-20 μl). The current-voltage characteristics were measured using an Agilent 4156C parameter analyzer with the gate region exposed.

Figure 23:
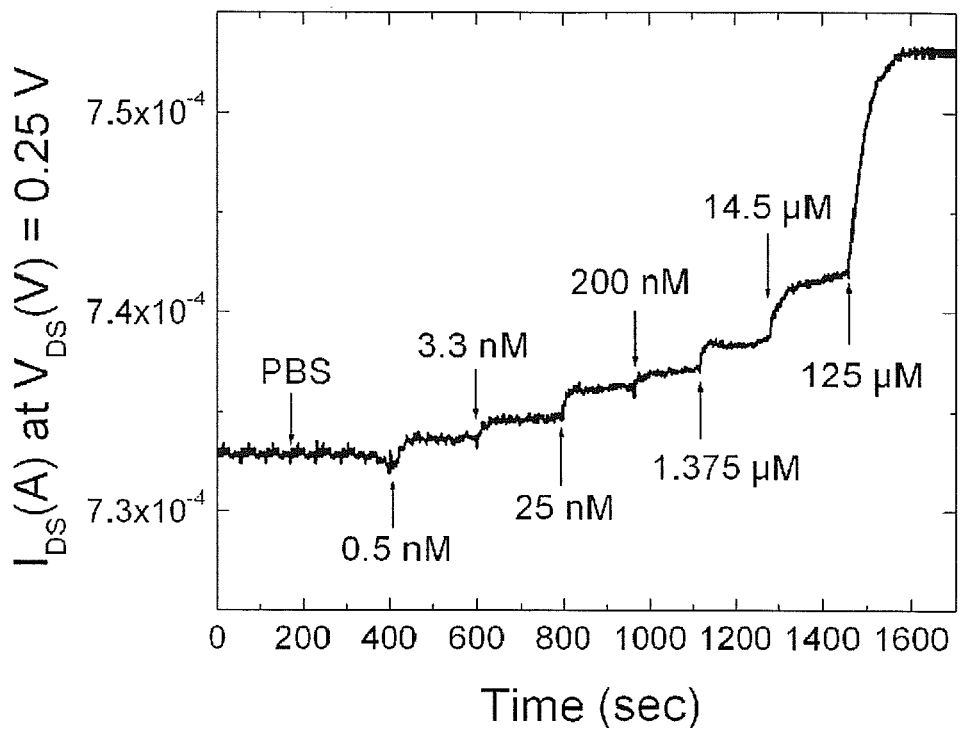
FIG. 23 shows plot of drain current versus time with successive exposure of glucose from 500 pM to 125 μM in 10 mM phosphate buffer saline with a pH value of 7.4.

FIG. 23 shows the real time glucose detection in PBS buffer solution using the drain current change with constant bias of 250 mV. No current change can be seen with the addition of buffer solution at around 200 sec, showing the specificity and stability of the device. By sharp contrast, the current change showed a rapid response in less than 5 seconds when target glucose was added to the surface. The response is very linear from 0.5 nM to 14.5 µM and showed an experimental limit of detection of 0.5 nM.

Figure 24:
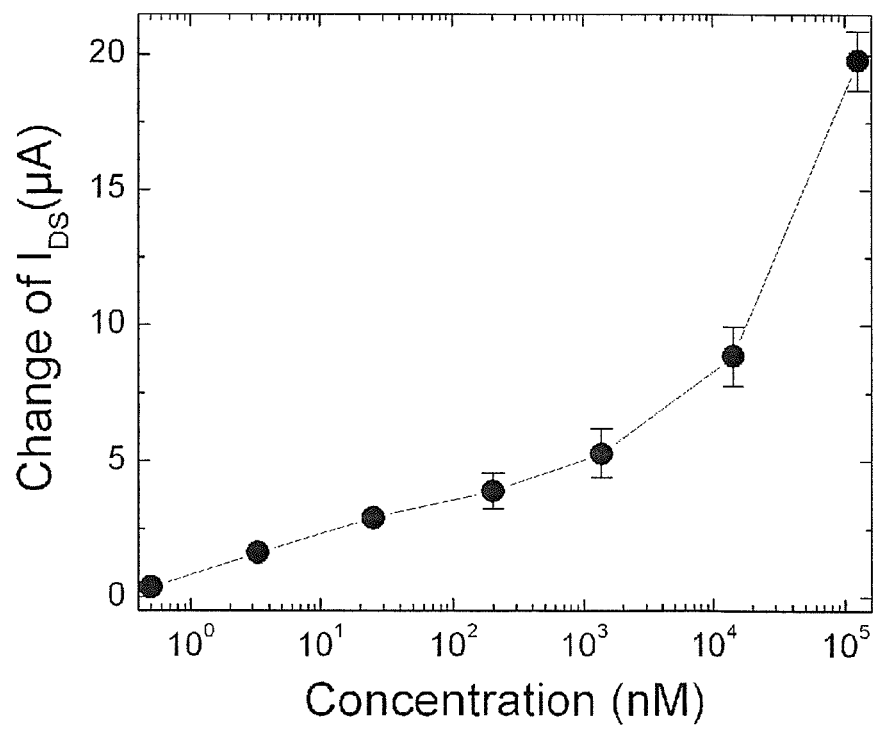
FIG. 24 shows plot of change of drain current as a function of glucose concentrations from 500 pM to 125 μM in 10 mM phosphate buffer saline with a pH value of 7.4.

Immobilization of the negatively charged GOx on the positively charged ZnO nanorod arrays is maximized around the pH value of 7.4 and reduces to about 80% for pH=5 to 6. Once the pH value is larger than 8, the activity drops significantly. The human pH value can vary depending on the health condition, e.g. the pH value for patients with acute asthma was reported as low as 5.23±0.21 (n=22) as compared to 7.65±0.20 (n=19) for the control subjects. In order to get accurate measurements of glucose concentration in the EBC, one needs to know the correlation of the pH value of the EBC and the sensitivity of GOx functionalized for specific sensors. The low detection limit of the sensor permitted dilution of <0.1 µ-liter of exhaled breath condensate (EBC) in 100-200 µ-liter PBS and the direct measurement of the glucose concentration to eliminate the effect of pH variation of the EBC. FIG. 24 shows the changes of drain current as a function of glucose concentration. A very good linear relationship of glucose concentration vs. drain current changes was obtained. Because of the fast response time and low volume of the EBC required, a handheld real-time glucose sensor can be made.

Figure 25A:
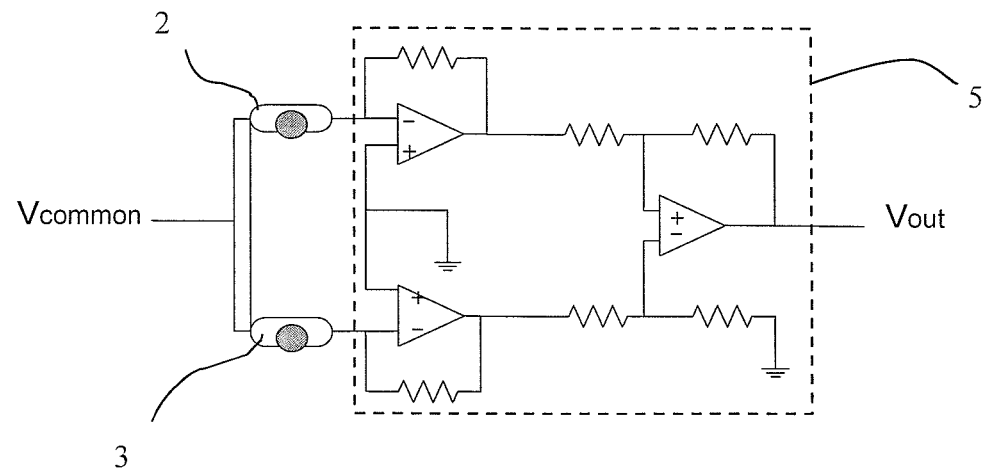
FIG. 25A shows a schematic diagram of a differential amplifier circuit that can be used to output the signal from the response of a normalized temperature sensor in accordance with an embodiment of the present invention.
Figure 25B:
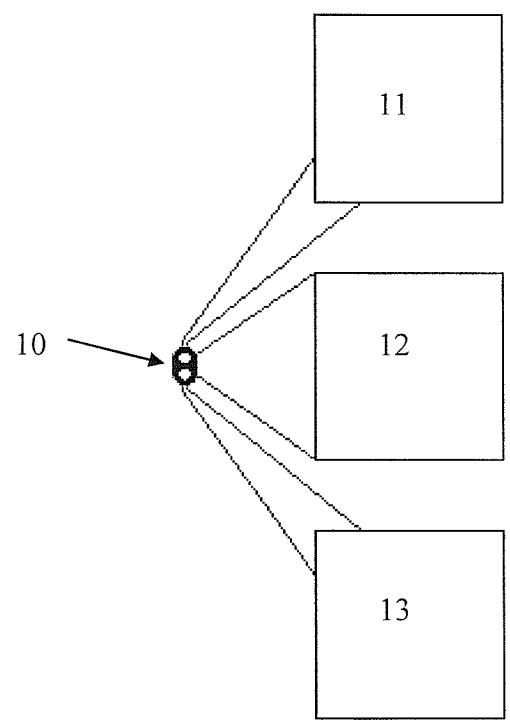
FIG. 25B shows a plan view schematic representation of contact pads for a normalized sensing device in accordance with an embodiment of the present invention.

Embodiments are provided for improved temperature response that utilize a normalized diode or field effect transistor (FET) configuration. According to an embodiment, a control sensor and an active sensor are arranged in a common ground configuration. A differential amplifier can be connected to the normalized HEMT-based sensor to provide an amplified output of the sensor's response to the target molecule in solution (i.e., the element being detected in the environment). The differential amplifier amplifies the difference between the two sensors and rejects the signal that is common to the inputs. For example, FIG. 25A shows a schematic representation of a normalized sensor output circuit 5 in accordance with one embodiment of the present invention. The control sensor 2 is connected to one input of the output circuit 5 and the active sensor 3 is connected to another input of the output circuit 5. The control sensor 2 and the active sensor 3 are also connected to a common node providing a common voltage $V_{common}$. In other embodiments, the schematic shown in FIG. 25A can be replaced with any suitable differential amplifier circuit. Though not shown in the figures, an initialization circuit can be included to reset the sensor and/or to bias the output circuit 5. Any suitable biasing circuit can be used. FIG. 25B shows contact pads for the sensor 10 according to one embodiment. A first contact pad 11 can connect the control sensor to the differential amplifier circuit; a second contact pad 12 can connect the common node of the control sensor and the active sensor to a ground signal; and a third contact pad 13 can connect the active sensor to the differential amplifier circuit.

In accordance with embodiments of the present invention, both the control and the active sensor are exposed to the ambient temperature. The control (or reference) sensor of an embodiment of the present invention has the exact same gate functionalization to semiconductor interface as the active sensor of the subject device. Further, the gate functionalization of the control sensor is covered with another layer, a layer with a similar binding functional group but different terminated functional group, or antibodies not sensitive to the designated detection. An example where the gate functionalization of the control sensor is covered with a layer with similar binding functional group but different terminated function group is using methyl mercaptans ($HS—CH_3$ or $HS—(CH_2)_n—CH_3$, where n=0, 1, 2, . . . ) for the reference sensor for Hg ion detection where thioglycolic acid ($HS—CH_2—CH_2—COOH$) is used for the active sensor.

The additional layer can be a protective layer of metal, dielectric, antibody, Bovine serum albumin (BSA), protein, aptamer, or polymer, which is inert to the element being detected in the surrounding environment or inhibits the gate functionalization material of the control sensor from being exposed to the element being detected in the surrounding environment.

According to an embodiment of the present invention, the sensing response signal is output from the potential difference between the control sensor and the active sensor. The source regions of the sensors are grounded together for diode mode sensing and the drain regions of the sensor are floated. If the FET mode is used for the sensing, the drain current or threshold voltage of the HEMT is used to monitor the concentration of the element being detected instead of diode current used in the diode mode sensing.

The normalized configuration provides a built-in control diode to reduce false alarms due to temperature swings or voltage transients. Since both the control and the active sensor have the same interface between the semiconductor material of the HEMT and the gate functionalization, the diode or FET characteristics will be substantially the same regardless of ambient temperature. Thus, the differences in diode or FET characteristics for the two sensors (control and active) occur only in their exposure to the environment. Specifically, the active sensor will respond to elements being detected in the environment and the control sensor will not.

The HEMT amplifies the signal detected from the gate of the active sensor, thereby enabling extremely sensitive sensing. The amplified signal of the active sensor can then be compared to the control sensor signal through, for example, the differential amplifier circuit of FIG. 25A to provide a normalized signal. In addition, embodiments of the present invention can accomplish these reductions in false alarms at a wide range of temperatures. In certain embodiments, the subject sensor can reduce false alarms for temperatures between −40° C. and 80° C.

According to embodiments of the present invention, a normalized diode configuration is provided where the control device includes the same HEMT interface structure as the gate functionalization of the active device, but further includes the metal of a final metal layer, dielectrics, antibody, BSA, protein, aptamer, or polymers.

Figure 26A:
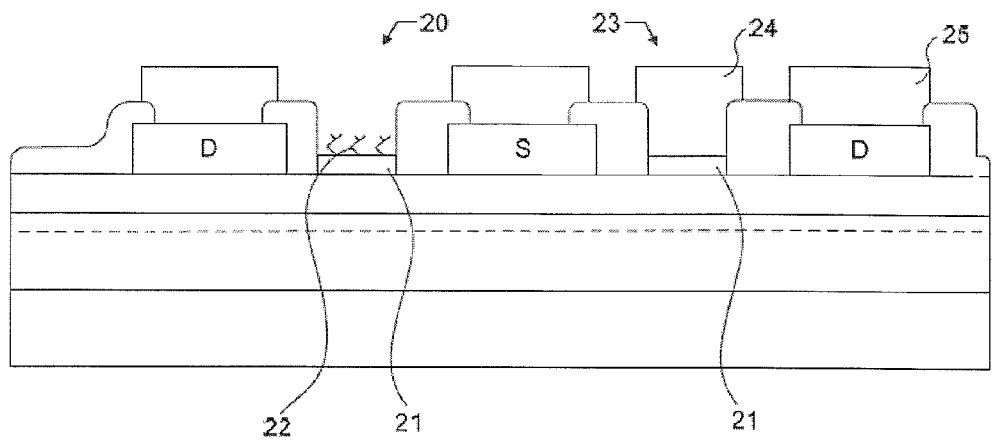
FIG. 26A shows a cross-sectional view of an active and control sensor configuration for a normalized sensing device for heavy metal detection in accordance with one embodiment of the present invention.

In one embodiment example, referring to FIG. 26A, for heavy metal detection, the active member 20 of the normalized pair has a gold-based gate contact 21 with a chelating agent 22 bonded thereto, and the control member 23 of the normalized pair has a gold-based gate contact 21 and a protective layer 24. The protective layer 24 can be a metal layer, a dielectric layer, antibody, BSA, protein, aptamer, methyl mercaptans ($HS—CH_3$ or $HS—(CH_2)_n—CH_3$), or a polymer layer. When a metal layer is used for the protective layer 24, it can be the metal layer(s) used for final metal contacts 25 of the device. In certain implementations of a heavy metal normalized sensor, the control sensor can be functionalized similarly to the active sensor by coating the reference sensor with the methyl mercaptans ($HS—CH_3$ or $HS—(CH_2)_n—CH_3$), metal, dielectric, or polymer instead of thioglycolic acid ($HS—CH_2—CH_2—COOH$).

Figure 26B:
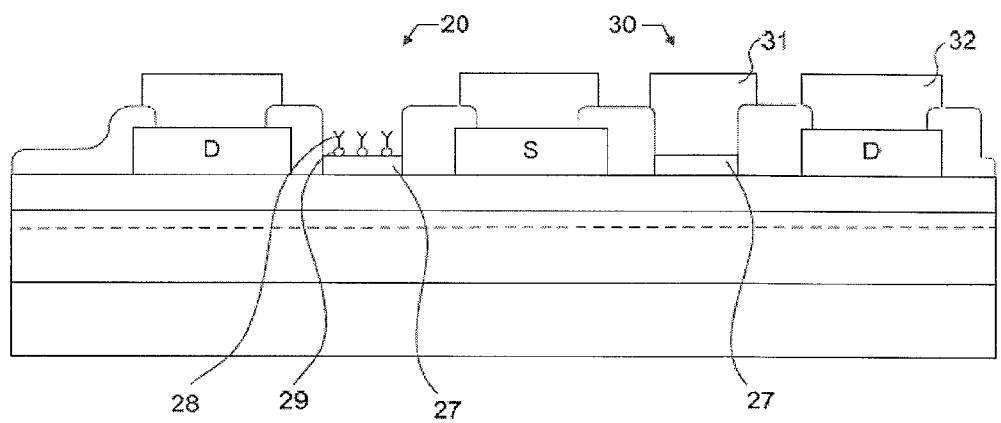
FIG. 26B shows a cross-sectional view of an active and control sensor configuration for a normalized sensing device for prostate cancer antigen detection in accordance with one embodiment of the present invention.

In another embodiment example, referring to FIG. 26B, for prostate specific antigen detection, the active member 26 of the normalized pair has a gold-based gate contact 27 with PSA antibody 28 anchored to the gate area with a binding agent 29 to the gold-based gate contact 27, and the control member 30 of the normalized pair has a gold-based gate contact 27 and a protective layer 31. The protective layer 31 can be a metal layer, a dielectric layer, antibodies not sensitive to the prostate specific antigen, BSA, protein, aptamer, methyl mercaptans (HS—$CH_3$ or HS—$(CH_2)_n$—$CH_3$), or a polymer layer. When a metal layer is used for the protective layer 31, it can be the metal layer(s) used for final metal contacts 32 of the device. In certain implementations of a PSA normalized sensor, the control sensor can be functionalized similarly to the active sensor by coating the gate area of the reference sensor with the metal, dielectric, antibodies not sensitive to the prostate specific antigen, BSA, protein, aptamer, methyl mercaptans (HS—$CH_3$ or HS—$(CH_2)_n$—$CH_3$), or polymer.

Figure 26C:
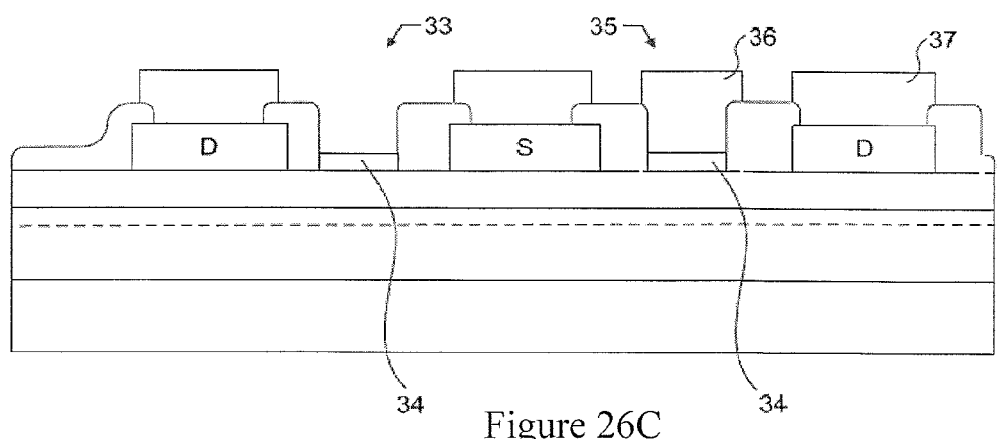
FIG. 26C shows a cross-sectional view of an active and control sensor configuration for a normalized sensing device for pH detection in accordance with one embodiment of the present invention.

In yet another embodiment example, referring to FIG. 26C, for detection of changes in pH in electrolyte solutions, the active member 33 of the normalized pair has a non-native oxide 34 on the gate region, and the control member 35 of the normalized pair has the non-native oxide 34 and a protective layer 36. The protective layer 36 can be a metal layer, another dielectric layer, or a polymer layer. When a metal layer is used for the protective layer 36, it can be the metal layer(s) used for final metal contacts 37 of the device.

Figure 26D:
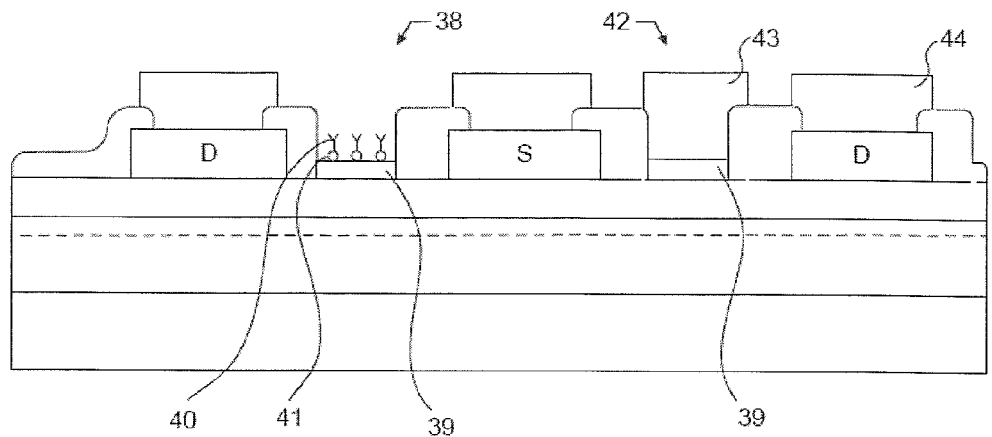
FIG. 26D shows a cross-sectional view of an active and control sensor configuration for a normalized sensing device for kidney injury molecule-1 detection in accordance with one embodiment of the present invention.

In another embodiment example, referring to FIG. 26D, for kidney injury molecule-1 detection, the active member 38 of the normalized pair has a gold-based gate contact 39 with KIM-1 antibody 40 anchored to the gate area with a binding agent 41 to the gold-based gate contact 39, and the control member 42 of the normalized pair has the gold-based gate contact 39 and a protective layer 43. The protective layer 43 can be a metal layer, a dielectric layer, antibodies not sensitive to the kidney injury molecule-1, BSA, protein, aptamer, methyl mercaptans (HS—$CH_3$ or HS—$(CH_2)_n$—$CH_3$), or a polymer layer. When a metal layer is used for the protective layer 43, it can be the metal layer(s) used for final metal contacts 44 of the device. In certain implementations of a KIM-1 normalized sensor, the control sensor can be functionalized similarly to the active sensor by coating the gate area of the reference sensor with the metal, dielectric, antibodies not sensitive to the kidney injury molecule-1, BSA, protein, aptamer, methyl mercaptans (HS—$CH_3$ or HS—$(CH_2)_n$—$CH_3$), or polymer.

Figure 26E:
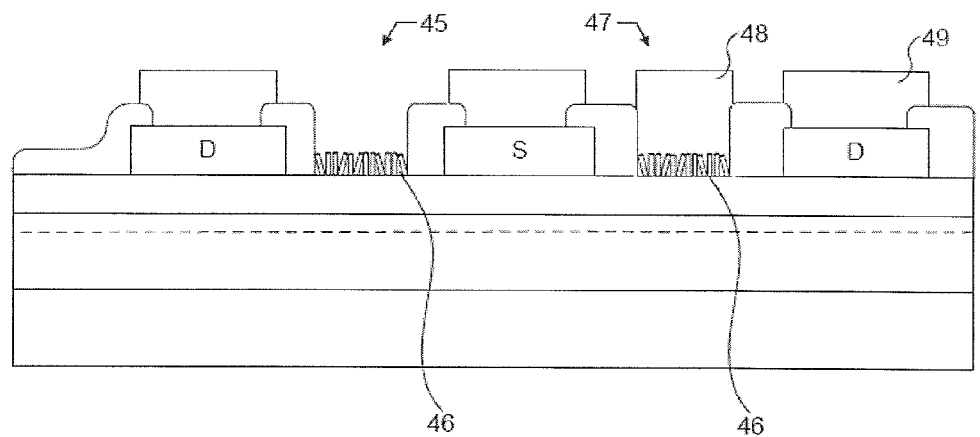
FIG. 26E shows a cross-sectional view of an active and control sensor configuration for a normalized sensing device for glucose detection in accordance with one embodiment of the present invention.

In one embodiment example, referring to FIG. 26E, for glucose detection, the active member 45 of the normalized pair has ZnO nanorods 46 on the gate region, and the control member 47 of the normalized pair has the ZnO nanorods 46 and a protective layer 48. The protective layer 48 can be a metal layer, an enzyme layer not sensitive to the glucose, a dielectric layer, or a polymer layer. When a metal layer is used for the protective layer 48, it can be the metal layer(s) used for final metal contacts 49 of the device.

Figure 26F:
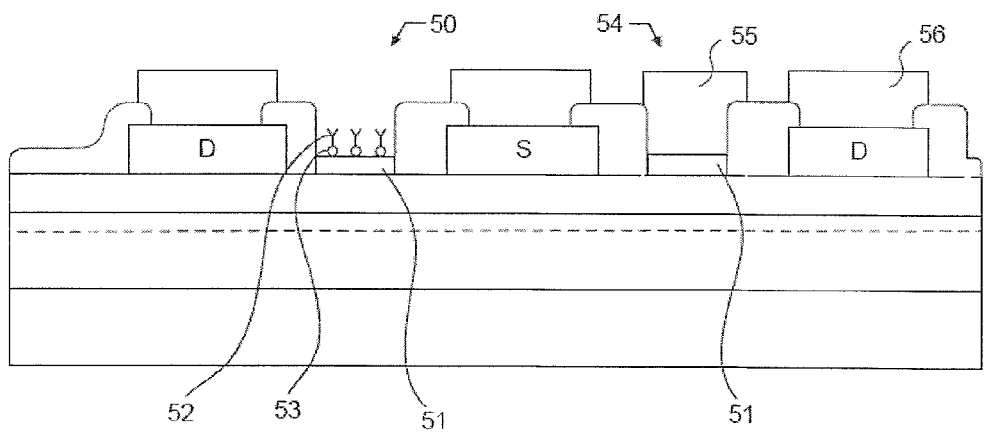
FIG. 26F shows a cross-sectional view of an active and control sensor configuration for a normalized sensing device for breast cancer antigen detection in accordance with one embodiment of the present invention.

In yet another embodiment example, referring to FIG. 26F, for breast cancer specific antigen detection, the active member 50 of the normalized pair has a gold-based gate contact 51 with breast cancer specific antibody 52, such as EGF, c-erbB-2, and CA15-3, anchored to the gate area with a binding agent 53 to the gold-based gate contact 51, and the control member 54 of the normalized pair has a gold-based gate contact 51 and a protective layer 55. The protective layer 55 can be a metal layer, a dielectric layer, antibodies not sensitive to the breast cancer specific antigen, BSA, protein, aptamer, methyl mercaptans (HS—$CH_3$ or HS—$(CH_2)_n$—$CH_3$), or a polymer layer. When a metal layer is used for the protective layer 55, it can be the metal layer(s) used for final metal contacts 56 of the device. In certain implementations of the normalized sensor, the control sensor can be functionalized similarly to the active sensor by coating the gate area of the reference sensor with the metal, dielectric, antibodies not sensitive to the breast cancer specific antigen, BSA, protein, aptamer, methyl mercaptans (HS—$CH_3$ or HS—$(CH_2)_n$—$CH_3$), or polymer.

Figure 27:
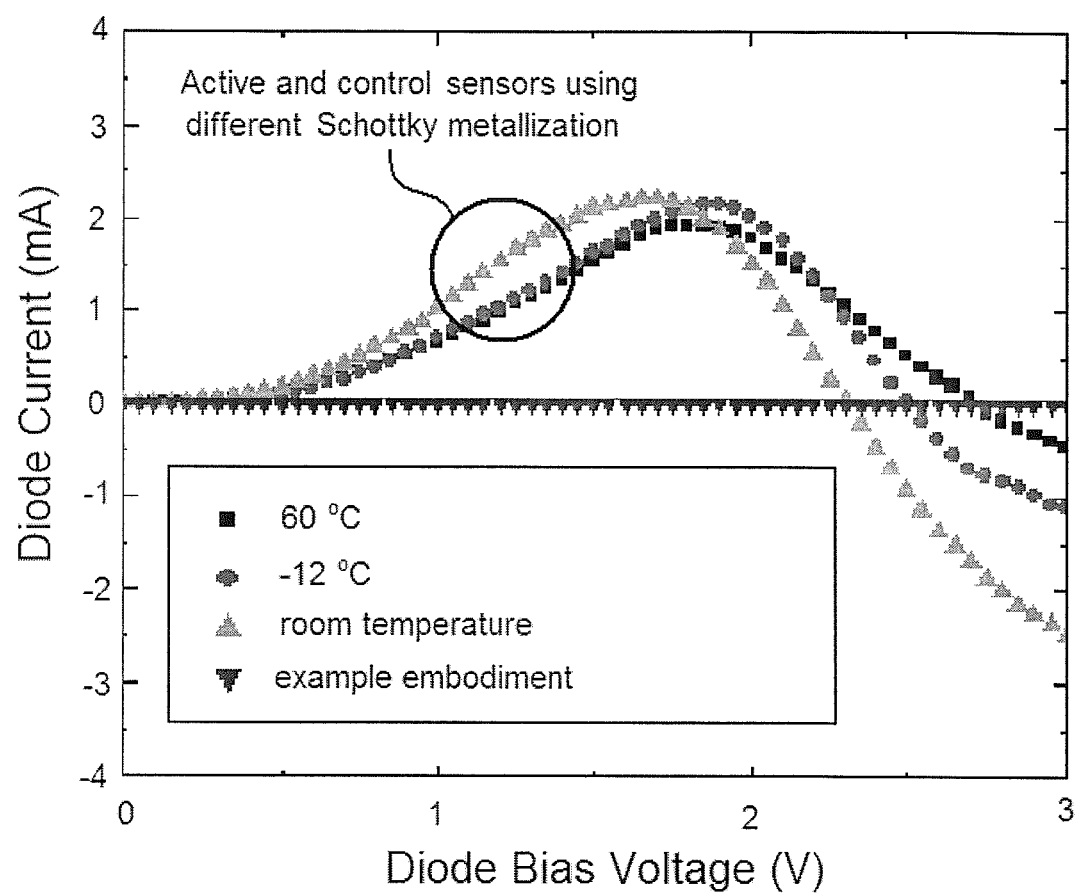
FIG. 27 shows a plot of diode current vs. bias voltage comparing a related art differential sensor to a normalized sensor in accordance with an embodiment of the present invention.

Advantageously, by providing both the control device and the active device with a same or similar gate functionalization, Schottky characteristics exist for both devices. In addition, the inclusion of the same gate functionalization to HEMT semiconductor interface for both the active device and the control device brings the work function of the control device in line with the active device, thereby making the response to different temperature ambients in line with each other and reducing the effects of having different responses to the different temperature ambients. This effect can be seen in FIG. 27. FIG. 27 shows a plot of the difference of diode current vs. bias voltage between a reference (control) and an active sensor for active and control sensors using different Schottky metallization at three temperature ambients compared to an example embodiment where the active and control sensors use a same Schottky metallization. It should be noted that these plots represent the current in an ambient environment having no element being detected. Therefore, for the sensing device of embodiments of the present invention, the temperature and bias dependence of the response signal can be minimized and the signal be normalized to indicate only the presence of the element being detected (as opposed to temperature dependence).

Specifically, as shown in FIG. 27, by not providing both the control device and the active device with a same or similar gate functionalization, the device where the control and active sensors use different Schottky metallization as the gate contact shows sensitivity to temperature changes and applied bias. In contrast, an embodiment of the present invention using same Schottky metallization as the gate contact is capable of maintaining a constant current over change in bias and temperature. As shown in the plot, even where a control diode is used (but does not have the same gate metal as the active diode), the difference of the diode current from the control and active diode is not zero (normalized). This is due to the gate metal/semiconductor interface of the control sensor being different from the active diode. The work function of the different metal/semiconductor interfaces is different and the diode current of the two sensors (control and active) would be different at different bias as well as different temperature.

All patents, patent applications, provisional applications, and publications referred to or cited herein are incorporated by reference in their entirety, including all Figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. An AlGaN/GaN high electron mobility transistor (HEMT) based sensor for one or more target molecules in a sample, the sensor comprising:
   an AlGaN/GaN high electron mobility transistor (HEMT) comprising an Au-comprising gate, a source, and a drain;
   at least one capture reagent on the Au-comprising gate of the AlGaN/GaN HEMT, wherein the capture reagent binds or otherwise associates with a breast cancer antigen; and
   a fixed bias voltage connected to the source,
   wherein the drain connects to a signal analyzer that indicates an amount of breast cancer antigen based on a change in drain current occurring solely from the capture reagent binding or otherwise associating with the breast cancer antigen when the fixed bias voltage is applied to the source.

2. The sensor of claim 1, wherein the capture reagent is an antibody to a breast cancer antigen selected from EGF, c-erbB-2, CA15-3, and any combination thereof.

3. The sensor of claim 2, wherein the AlGaN/GaN HEMT is provided in plurality on a single chip, wherein each HEMT has at least one of the breast cancer antigens on its gate region, wherein at least two of the HEMTs have different breast cancer antigens.

4. The sensor of claim 1, further comprising a binding group layer to couple the capture reagent to the Au-comprising gate.

5. The sensor of claim 1, wherein the binding group layer comprises thioglycolic acid.

6. The sensor of claim 1, further comprising at least one wireless communication circuit on a chip, wherein the AlGaN/GaN HEMT comprises an array of HEMTs on the chip, and wherein a signal from the sensor is wirelessly transmittable via the at least one wireless communication circuit.

7. The sensor of claim 1, further comprising a control HEMT connected to a source region of the AlGaN/GaN HEMT, wherein the control HEMT includes the Au-comprising gate and a protective layer covering the Au-comprising gate.

8. The sensor of claim 7, wherein the protective layer comprises a metal layer, a dielectric layer, antibodies not sensitive to the breast cancer antigen, BSA, protein, aptamer, methyl mercaptans ($HS-CH_3$ or $HS-(CH_2)_n-CH_3$), or a polymer layer.

9. The sensor of claim 8, wherein the protective layer is the metal layer, wherein the metal layer comprises metal of final metal contacts of the sensor.

10. The sensor of claim 1, wherein the sensor is a portable or hand-held saliva based breast cancer sensor.

11. A method of detecting a target molecule in a sample comprising:
providing a sample suspected of containing a target molecule;
contacting the sample with a sensor comprising an AlGaN/GaN high electron mobility transistor (HEMT) comprising an Au-comprising gate, a source, and a drain; and at least one capture reagent on the Au-comprising gate of the AlGaN/GaN HEMT; and
applying a fixed bias voltage to the source,
wherein a signal is generated by the sensor when the target molecule is present in the sample and interacts with the capture reagent,
wherein the sample is saliva, the target molecule is a breast cancer antigen, and the capture reagent is an antibody to the breast cancer antigen,
wherein the breast cancer antigen is identified by a change in drain current occurring solely from the capture reagent binding or otherwise associating with the breast cancer antigen when the fixed bias voltage is applied to the source.

12. The method of claim 11, wherein the sensor further comprises a binding agent layer to couple the antibody to the Au-comprising gate.

13. The method of claim 12, wherein the binding group layer comprises thioglycolic acid.

14. The method of claim 11, wherein the capture reagent is selected from EGF, c-erbB-2, CA15-3, and any combination thereof.

15. The method of claim 14, wherein the HEMT is provided in plurality, wherein each HEMT has at least one of the breast cancer antigens on its gate region, wherein at least two of the HEMTs have different breast cancer antigens.

16. The method of claim 11, wherein the sensor further comprises at least one wireless communication circuit on a chip, wherein the HEMT comprises an array of HEMTs on a chip, and wherein the signal is wirelessly transmittable.

17. The method of claim 16, further comprising the step of transmitting wirelessly the signal to a receiver for the signal.

18. The method of claim 11, wherein the sensor is a portable or hand-held saliva based breast cancer sensor.

19. The method of claim 11, further comprising a control HEMT connected to a source region of the AlGaN/GaN HEMT, wherein the control HEMT includes the Au-comprising gate and a protective layer covering the Au-comprising gate,
wherein a normalized signal is generated by the sensor when the target molecule is present in the sample and interacts with the capture reagent.

20. The method of claim 19, wherein the protective layer comprises a metal layer, a dielectric layer, antibodies not sensitive to the breast cancer antigen, BSA, protein, aptamer, methyl mercaptans ($HS-CH_3$ or $HS-(CH_2)_n-CH_3$), or a polymer layer.

* * * * *